(12) United States Patent
McErlean et al.

(10) Patent No.: US 11,980,769 B2
(45) Date of Patent: May 14, 2024

(54) STENOSIS TREATMENT

(71) Applicant: Emblation Limited, Scotland (GB)

(72) Inventors: Eamon McErlean, Alloa (GB); Gary Beale, Dunblane (GB); Matthew Donald Kidd, Stirling (GB)

(73) Assignee: EMBLATION LIMITED

( * ) Notice: Subject to any disclaimer, the term of this patent is extended or adjusted under 35 U.S.C. 154(b) by 214 days.

(21) Appl. No.: 15/938,238

(22) Filed: Mar. 28, 2018

(65) Prior Publication Data
US 2018/0280715 A1  Oct. 4, 2018

Related U.S. Application Data

(60) Provisional application No. 62/477,816, filed on Mar. 28, 2017.

(51) Int. Cl.
| | | |
|---|---|---|
| A61N 5/02 | (2006.01) | |
| A61F 2/82 | (2013.01) | |
| A61K 41/00 | (2020.01) | |
| A61N 5/04 | (2006.01) | |
| A61P 9/10 | (2006.01) | |
| A61B 18/18 | (2006.01) | |
| A61M 25/10 | (2013.01) | |

(52) U.S. Cl.
CPC .............. *A61N 5/025* (2013.01); *A61F 2/82* (2013.01); *A61K 41/0052* (2013.01); *A61N 5/045* (2013.01); *A61P 9/10* (2018.01); *A61B 2018/1861* (2013.01); *A61M 25/10* (2013.01)

(58) Field of Classification Search
CPC . A61N 5/025; A61N 5/045; A61P 9/10; A61F 2/82; A61K 41/0052; A61B 2018/1861; A61M 25/10
See application file for complete search history.

(56) References Cited

U.S. PATENT DOCUMENTS

| | | |
|---|---|---|
| 4,149,170 A | 4/1979 | Campbell et al. |
| 4,517,975 A | 5/1985 | Garito et al. |
| 4,914,717 A | 4/1990 | Gibbon |
| 5,091,707 A | 2/1992 | Wollmerschauser et al. |
| 5,195,965 A | 3/1993 | Shantha |
| 5,272,301 A | 12/1993 | Finger et al. |
| 5,507,791 A | 4/1996 | Sit'ko |
| 5,649,973 A | 7/1997 | Tierney et al. |
| 5,683,386 A | 11/1997 | Ellman et al. |

(Continued)

FOREIGN PATENT DOCUMENTS

| | | |
|---|---|---|
| CN | 1277879 | 12/2000 |
| CN | 102905639 | 1/2013 |

(Continued)

OTHER PUBLICATIONS

Smith et al. "Microwave thermal balloon angioplasty in the normal rabbit," American Heart Journal, Jun. 1992, vol. 123, No. 6, pp. 1516-1521.

(Continued)

*Primary Examiner* — Sean W Collins
*Assistant Examiner* — Rachel A. Vierra
(74) *Attorney, Agent, or Firm* — Sheridan Ross P.C.

(57) ABSTRACT

Heat and heat based treatments that may be used to modulate, inhibit and/or prevent one or more of the processes that contribute to certain vascular and/or arterial complications.

11 Claims, 16 Drawing Sheets

(56) References Cited

U.S. PATENT DOCUMENTS

Figure 1:
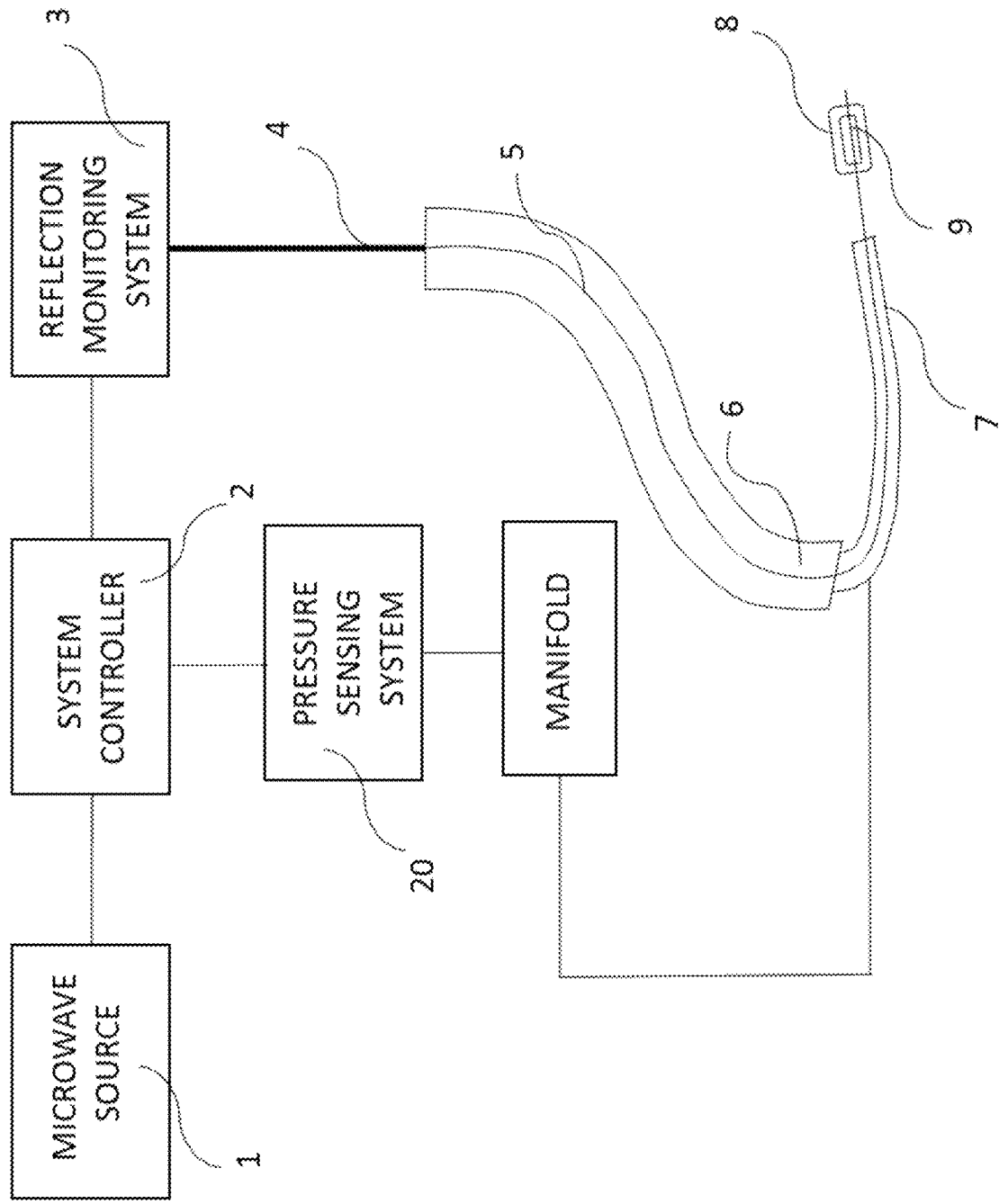

| | | | |
|---|---|---|---|
| 5,879,379 | A | 3/1999 | Mason et al. |
| 5,993,480 | A | 11/1999 | Burrows |
| 6,047,216 | A * | 4/2000 | Carl .................. A61B 18/1492 |
| | | | 607/101 |
| 6,104,959 | A | 8/2000 | Spertell |
| 6,710,673 | B1 | 3/2004 | Jokerst |
| 7,052,283 | B2 | 5/2006 | Pixley et al. |
| 7,211,411 | B2 | 5/2007 | Neefe et al. |
| 7,292,893 | B2 | 11/2007 | Hoenig et al. |
| 7,981,112 | B1 | 7/2011 | Neev |
| 9,498,284 | B2 | 11/2016 | McErlean et al. |
| 9,543,061 | B2 | 1/2017 | McErlean et al. |
| 9,662,510 | B2 | 5/2017 | Beale et al. |
| 2001/0050605 | A1 | 12/2001 | Suggiura et al. |
| 2003/0012830 | A1 | 1/2003 | Small |
| 2003/0225441 | A1 | 12/2003 | Boynton et al. |
| 2004/0202663 | A1 | 10/2004 | Hu et al. |
| 2005/0251231 | A1 | 11/2005 | Goldberg |
| 2006/0020312 | A1 | 1/2006 | Eggers et al. |
| 2006/0235286 | A1 * | 10/2006 | Stone .................. A61B 5/053 |
| | | | 600/381 |
| 2006/0265034 | A1 | 11/2006 | Aknine et al. |
| 2008/0149100 | A1 | 6/2008 | Van Holst et al. |
| 2008/0183164 | A1 | 7/2008 | Elkins et al. |
| 2008/0294073 | A1 | 11/2008 | Barthe et al. |
| 2008/0319517 | A1 | 12/2008 | Cumbie |
| 2010/0010480 | A1 | 1/2010 | Mehta et al. |
| 2010/0036369 | A1 | 2/2010 | Hancock |
| 2010/0114086 | A1 | 5/2010 | Deem et al. |
| 2010/0211059 | A1 | 8/2010 | Deem et al. |
| 2012/0016356 | A1 | 1/2012 | Beale et al. |
| 2012/0203218 | A1 | 8/2012 | Bonn |
| 2013/0178383 | A1 | 7/2013 | Spetzler et al. |
| 2013/0190750 | A1 | 7/2013 | Behnke et al. |
| 2013/0282084 | A1 * | 10/2013 | Mathur .............. A61B 18/1492 |
| | | | 607/101 |
| 2014/0066837 | A1 | 3/2014 | Moy |
| 2014/0249601 | A1 | 9/2014 | Bachinski et al. |
| 2014/0356397 | A1 | 12/2014 | Akle et al. |
| 2015/0024961 | A1 | 1/2015 | Klass et al. |
| 2015/0080875 | A1 * | 3/2015 | Kasprzyk ........... A61B 18/1815 |
| | | | 606/33 |
| 2016/0022976 | A1 | 1/2016 | Peyman |
| 2016/0324577 | A1 | 11/2016 | Beale et al. |
| 2017/0056106 | A1 | 3/2017 | McErlean et al. |
| 2018/0036551 | A1 | 2/2018 | McErlean et al. |
| 2019/0069949 | A1 * | 3/2019 | Vrba .................... A61B 17/122 |
| 2019/0255348 | A1 | 8/2019 | Beale et al. |
| 2019/0274758 | A1 | 9/2019 | Beale et al. |
| 2020/0353278 | A1 | 11/2020 | McErlean et al. |
| 2020/0398084 | A1 | 12/2020 | Guha et al. |

FOREIGN PATENT DOCUMENTS

| | | |
|---|---|---|
| EP | 2485326 | 8/2012 |
| JP | 2010-507403 | 3/2010 |
| JP | 2012-506300 | 3/2012 |
| JP | 2012-508062 | 4/2012 |
| JP | 2013-523346 | 6/2013 |
| JP | 2013-525075 | 6/2013 |
| JP | 2014-531935 | 12/2014 |
| JP | 2015-037587 | 2/2015 |
| JP | 2016-010729 | 1/2016 |
| JP | 2016-501575 | 1/2016 |
| WO | WO 91/03207 | 3/1991 |
| WO | WO 93/22977 | 11/1993 |
| WO | WO 98/49933 | 11/1998 |

OTHER PUBLICATIONS

"Phenol," HPA Compendium of Chemical Hazards, 2011, Version 4, 32 pages.

Bevans et al. "A comparison of electrosurgery and sharp debridement in the treatment of chronic neurovascular, neurofibrous and hard corns. A pragmatic randomised controlled trial," The Foot, Mar. 2010, vol. 20, No. 1, pp. 12-17.

Cavaliere "Treatment of Porokeratosis Plantaris Discreta," The Podiatry Institute, (Predilection and Clinical Assessment), 1993, pp. 145-149 [retrieved online from: www.poodiatryinstitute.com/pdfs/update_1993/1993_28.pdf].

Chapeskie, "Ingrown Toenail or overgrown toe skin?" Canadian Family Physician, 2008, vol. 54, No. 11, pp. 1561-1562.

Choi et al. "Short-Term Heat Exposure Inhibits Inflammation by Abrogating Recruitment of and Nuclear Factor-κB Activation in Neutrophils Exposed to Chemotactic Cytokines." The American Journal of Pathology, 2008, vol. 172(2), pp. 367-377.

Clayton et al., Patty's Industrial Hygiene and Toxicology, 3rd Edition, J Wiley and Sons, New York, 1982, p. 2583.

Coughlin "Common Causes of Pain in the Forefoot in Adults," The Journal of Bone & Joint Surgery (Br), Aug. 2000, vol. 82-B, No. 6, pp. 781-790.

De Pomerai et al. "Growth and maturation of the nematode Caenorhabditis elegans following exposure to weak microwave fields." Enzyme and Microbial Technology, 2002, vol. 30(1), pp. 73-79.

Fausch et al. "Human Papillomavirus Can Escape Immune Recognition through Langerhans Cell Phosphoinositide 3-Kinase Activation." The Journal of Immunology, 2005, vol. 174(11), pp. 7172-7178.

Gao et al. "Non-ablative controlled local hyperthermia for common warts." Chinese Medical Journal, 2009, vol. 122(17), pp. 2061-2063.

Hong-Xia et al. "Detection with the Polymerase Chain Reaction of Human Papillomavirus DNA in Condylomata Acuminata Treated with CO2 Laser and Microwave," International Journal of Dermatology, Mar. 1995, vol. 34, No. 3, pp. 209-211.

Kashima et al. "Polymerase chain reaction identification of human papillomavirus DNA in CO2 laser plume from recurrent respiratory papillomatosis." Otolaryngology Head Neck Surgery, 1991, vol. 104(2), pp. 191-195.

Koltaj "Er:YAG Laser Treatment of Intractable Plantar Keratosis (IPK)," Journal of the Laser and Health Academy, May 2013, vol. 2013, No. 1, pp. 32-35 [retrieved online from: https://www.laserandhealthacademy.com/media/objave/academy/priponke/32_35_koltaj_intractable_plantar_keratosis_jlaha_2013_1.pdf].

Li et al. "Detection with the Polymerase Chain Reaction of Human Papillomavirus DNA in Condylomata Acuminata Treated with CO2 laser and Microwave." International Journal of Dermatology, 1995, vol. 34(3), pp. 209-211.

Lipke "An Armamentarium of Wart Treatments," Clinical Medicine & Research, 2006, vol. 4(4), pp. 273-293.

Ogura et al. "Microwave hyperthermia treatment increases heat shock proteins in human skeletal muscle," British Journal of Sports Medicine, 2007, vol. 41, pp. 453-455.

Parker et al. "Specifying a Ferrite for EMI Suppression," Conformity, Jun. 2008, pp. 50-59.

Skitzki et al. "Hyperthermia as an immunotherapy strategy for cancer." Current Opinion in Investigational Drugs, Jun. 2009, vol. 10(6), pp. 550-558.

Tonomura et al. "Effects of Heat Stimulation via Microwave Applicator on Cartilage Matrix Gene and HSP70 Expression in the Rabbit Knee Joint." Journal of Orthopaedic Research, 2008, vol. 26(1), pp. 34-41.

"FAQ," Celsius42 Gmbh, as of Oct. 3, 2018, 19 pages [retrieved online Nov. 14, 23 from: web.archive.org/web/20181003195031/https://celsius42.de/de/faq].

Dianzani et al., "Cutaneous Human Papillomaviruses as Recurrence Factor in Actinic Keratoses," Int'l J. Immunopathology and Pharmacology, 2008, vo. 21(1), pp. 145-152.

Fink "Chaperone-Mediated Protein Folding," Physiological Reviews, 199, vol. 79, No. 2, pp. 425-449.

Jaattela "Heat Shock Proteins as Cellular Lifeguards," Annals of Medicine, 1999, vol. 31, No. 4, pp. 261-271.

Multhoff "Heat Shock Protein 70 (Hsp70): Membrane Location, Export and Immunological Relevance," Methods, 2007, vol. 42, No. 3, pp. 229-237.

(56) References Cited

OTHER PUBLICATIONS

Solanki et al. "Reduced Necrosis and Content of Apoptotic M1 Macrophages in Advanced Atherosclerotic Plaques of Mice With Macrophage-Specific Loss of Trpc3," Scientific Reports, 2017, vol. 7, Article 42526, 11 pages.
Vega et al. "Hsp70 Translocates into the Plasma Membrane after Stress and Is Released into the Extracellular Environment in a Membrane-Associated Form That Activates Macrophages," The Journal of Immunology, 2008, vol. 180, No. 6, pp. 4299-4307.
Zhang et al. "Hyperthermia on Immune Regulation: A Temperature's Story," Cancer Letters, 2008, vol. 271, No. 2, pp. 191-204.

* cited by examiner

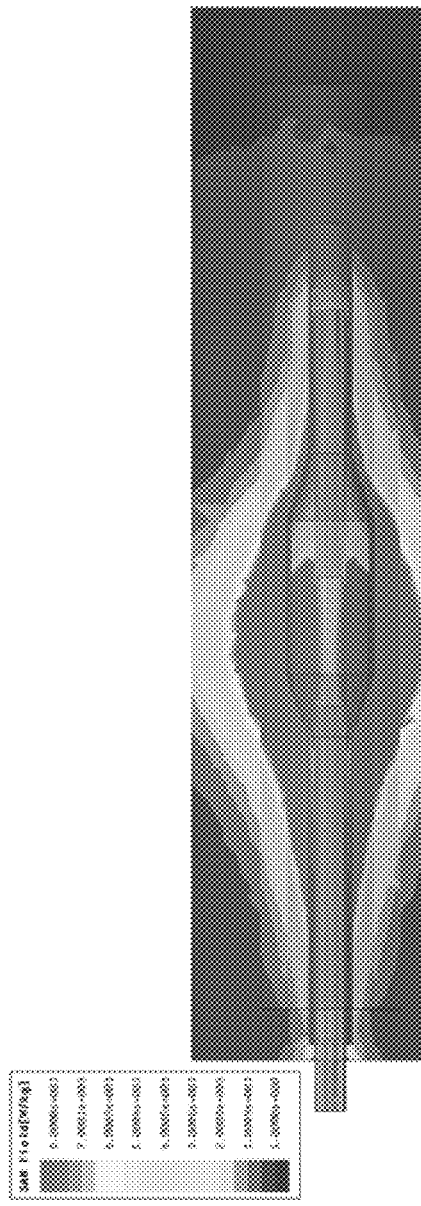

STENOSIS TREATMENT

CROSS REFERENCE TO RELATED APPLICATION

This application claims the benefit of priority under 35 U.S.C. § 119(e) to U.S. Provisional Patent Application Ser. No. 62/477,816, filed Mar. 28, 2017, which is incorporated herein by reference.

FIELD OF THE INVENTION

Described herein are methods, apparatus (devices) and uses which may be applied to the treatment, prevention and/or modulation of vascular and/or arterial complications including, for example, atherosclerosis, in-stent restenosis, peripheral arterial disease and peripheral vascular disease.

BACKGROUND

Atherosclerosis is a syndrome primarily caused by the inflammatory response in blood vessels (in particular arteries) to the build-up of lipids, cholesterol crystals and calcified plaques. Without treatment these vessels can become blocked, either by the build-up of deposited lipids, cholesterol crystals and plaques or through the formation and subsequent rupture of, a thrombus. Thrombus rupture can lead to a clot either at the site of an atherosclerotic plaque or further downstream, causing a cerebral infarction (stroke) if in the carotid artery or acute myocardial infarction (MI) commonly known as a heart attack if it is the cardiac arteries that are affected.

There is no known therapy to reverse Atherosclerosis. Interventions can be made to slow the rate of progression and reduce the risk of subsequent events through non-interventional methods e.g. managing blood pressure, diet and lifestyle. For example, pharmacological interventions can be made to reduce the levels of cholesterol, blood pressure and risk of blood clotting; physical interventions can be made to by-pass affected areas using graft vessels—however, in the case of the heart, this is a complex operation.

Should the myocardial infarction be diagnosed in conjunction with an electrocardiogram where an ST segment elevation is observed, this represents an emergency condition treated by coronary angioplasty (also known as percutaneous transluminal coronary angioplasty (PTCA). The procedure is also carried out by elective surgery in the case of a patient with stable angina, also caused by Atherosclerosis. PTCA uses a catheter inserted into an artery through an incision in the groin, wrist or arm. Under local anaesthetic, this is guided to the affected coronary artery using real-time X-ray imaging. When the catheter is in place, a thin wire is guided down the length of the affected coronary artery, delivering a small balloon to the affected section of artery. This is then inflated with fluid to enlarge the artery internal diameter, remodelling the lesion site by flattening the inflammation and plaque. After maintaining inflation pressure, for a minute so, the balloon is collapsed, and blood can flow through the lesion site with less lumen loss of inner diameter. When PTCA uses a balloon that has no special features such as a drug eluting surface or cutting elements then it is known as a "Plain Old Balloon Angioplasty" or POBA.

Due to natural elastic recoil, PTCA is not a long-lasting solution, with occlusions reforming or resistance to flow experienced in the majority of cases. A permanent addition of a physical support with a mesh metallic tube, or stent is frequently augmented with PTCA and is usually referred to as percutaneous coronary intervention (PCI). The material of the stent may be uncoated (a so-called bare metal stent (BMS)) or have pharmacologically active polymers on the surface (referred to as drug eluting stents (DES)).

However, the embedding of a foreign object into the vessel wall creates irritation and the inflammation response can be similar to the initial atherosclerosis in that growth into the lumen restricts blood flow and the stent benefit is undermined within months or years of fitting depending on other underlying environmental factors. This lumen loss is referred to as in-stent restenosis (ISR). The active coatings on a DES are designed to reduce the risk of ISR by inhibiting certain cell growth types and supressing the local immune response.

Atherosclerosis in other arteries of the body away from the heart can also follow the same aetiology. Areas treated with the same methodology of balloon and stent include carotid, aorta, iliac, femoral, popliteal and tibial arteries. When only the arteries are affected the condition is referred to as peripheral arterial disease (PAD) but if the veins are also affected then the state is referred to as peripheral vascular disease (PVD). Much in the same way as muscles downstream of the occlusion are affected in the cardiac case which leads to angina and MI, the brain or leg can become damaged from lack of oxygenated blood and cause stroke or gangrene respectively. In developed countries 20% of people over 75 are affected.

The process that mediates atherosclerotic plaque initiation and subsequent growth over many years involves an intricate interaction between smooth muscle cells, endothelial cells, monocyte-derived macrophages and groups of cytokines and inflammatory mediators that exist in the atheroma. Macrophages are known to be key components throughout all stages of atherosclerosis. However, the activated macrophage population is composed of 2 phenotypes with functionally distinct subsets: M1 (stimulated by TLR ligands and IFN-γ) known to be pro-inflammatory; whilst M2 (stimulated by IL-4 or IL-13) are anti-inflammatory by producing IL-10 factors. The ratio of the types varies during the lesion development and conversion is also known to occur (Solanki, Sumeet, et al. "Reduced Necrosis and Content of Apoptotic M1 Macrophages in Advanced Atherosclerotic Plaques of Mice with Macrophage-Specific Loss of Trpc3," Scientific Reports, vol. 7, 2017, p. 42526).

Macrophages are recruited into the arterial wall because of trapped cholesterol-rich lipoproteins. Early-stage lesions exhibit macrophage phagocytosis and disposal of small quantities of retained lipoproteins. However, this "efferocytosis" process ceases to be efficient and the maladaptive macrophage apoptosis cycle is at the crux of sustaining the atheroma and subsequent progression. The accumulation of apoptotic bodies leads to the growth of the necrotic core, mostly through secondary necrosis, formation of foam cells and induction of a further inflammatory response which fails to deal with the compounded inability to remove either lipoproteins or stalled macrophages.

Halting the progression of atherosclerotic lesions and/or even inducing their regression are highly desirable goals. Attempts to remove the atheroma in the clinical setting have been focussed on mechanical methods of drilling or scraping using a PCTA set up. A number of pharmacological routes are being investigated to reverse the plaque build-up. Lowering the amount of free circulating cholesterol lipids reduces the growth rate and can reverse the size of the plaque burden in the vessel as the body returns to equilibrium and the immune system becomes more effective at lipid removal within the atheroma. The efficacy of this process is affected by stage of atherosclerosis development, with earlier treatment more effective.

Fever is caused by the acute inflammatory response triggered by the body's immune system as a part of its host defence mechanism to fight infectious agents, environmental stresses, certain medications, malignancy etc. Fever has also been found to be closely correlated to spontaneous tumour regression. Deliberately raising a patient's body temperature to treat various conditions has been in practice since 18th century (Zhang, Hua-Gang, et al. "Hyperthermia on Immune Regulation: A Temperature's Story," Cancer Letters, vol. 271, no. 2, 2008, pp. 191-204). In recent years hyperthermia (HT) in conjunction with other established techniques prior to, or after (radio- and chemo-therapies), has been used extensively in numerous university hospitals to treat cancer. Fundamentally, HT can be active or passive. In active HT, body temperature is increased using bacterial toxins or by influencing the cytokines i.e. the fever is induced. Alternatively, passive HT (more common) comprises introducing heat externally through energy dissipation. Furthermore, HT can be classified into whole body HT, surface HT, locoregional HT, perfusion HT and interstitial HT (Celsius, G., 2017, celsius42.de/faq-2/?lang=en, [Online] [Accessed 16 03 2017]). The primary effects of HT on human body centre on the innate and adaptive immune systems.

It is established that heat shock proteins (HSPs) are produced in response to various tissue stresses or damage resulting from physical or environmental influences. Heat shock proteins are a class of functionally related proteins whose expression is increased when cells are exposed to elevated temperatures or other stress. It has been suggested that heat shock proteins may protect the cells from other stressors or against further damage by assisting in the refolding of damaged proteins (Fink, Anthony L. "Chaperone-Mediated Protein Folding," Physiological Reviews, vol. 79, no. 2, 1999, pp. 425-449). Heat shock proteins are also involved in antigen presentation, steroid receptor function, intracellular trafficking, nuclear receptor binding, and apoptosis. Typically, exposure of cells to heat shock temperatures in excess of 41 degrees C. results in transient activation of heat shock factor (HSF). The DNA-binding activity increases, plateaus, and dissipates, during which the intracellular levels of HSP increase. HSPs are classed as intracellular proteins but are also found in the extracellular environment thus they have dual functions.

Intracellular HSPs have a cytoprotective function which allows cells to survive lethal conditions. Intracellular HSPs increase secretion of IL-10 and can inhibit pro-inflammatory cytokine production i.e. anti-inflammatory effect. Intracellular HSPs diminish activation, maturation and survival of other cells such as dendritic cells (DCs); other anti-apoptotic functions of HSPs have been reported including preventing the release of pro-apoptotic factors such apoptosis inducing factor from the mitochondria.

Extracellular HSP interact with the immune system in complex methods. Free form extracellular HSPs are located in plasma for example or can be membrane bound, both mediate immunological responses and with positive or negative impacts on immunity function, depending on HSP family (mass) and cellular milieu. Additionally, HSP70 is involved in binding antigens and presenting them to the immune system (Multhoff, Gabriele. "Heat Shock Protein 70 (Hsp70): Membrane Location, Export and Immunological Relevance," Methods, vol. 43, no. 3, 2007, pp. 229-237; Vega, V. L., et al. "Hsp70 Translocates into the Plasma Membrane after Stress and is Released into the Extracellular Environment in a Membrane-Associated Form That Activates Macrophages," The Journal of Immunology, vol. 180, no. 6, 2008, pp. 4299-307).

Research into the physiological heating effects of electromagnetic fields has shown that high frequency microwave energy (existing between 500 MHz to 200 GHz) thermally produces elevated levels of specific heat shock proteins in tissue; see for example Ogura, Y., et al. (Ogura, Y., et al., "Microwave Hyperthermia Treatment Increases Heat Shock Proteins in Human Skeletal Muscle*COMMENTARY," British Journal of Sports Medicine, vol. 41, no. 7, 2007, pp. 453-455) that teaches that HSP90, HSP72, HSP27 levels are significantly higher in heated vastus lateralis muscle compared with unheated controls and Tonomura et al. (Tonomura, Hitoshi, et al. "Effects of Heat Stimulation via Microwave Applicator on Cartilage Matrix Gene and HSP70 Expression in the Rabbit Knee Joint," Journal of Orthopaedic Research, vol. 26, no. 1, 2008, pp. 34-41) which teaches that in vivo HSP70 expression in rabbit cartilage increases with the application of moderate levels of microwave power (20-40 W).

Hyperthermia also increases the expression of key adhesion molecules in secondary lymphoid tissues. Additionally, hyperthermia can also act directly on lymphocytes to improve their adhesive properties. Hyperthermia increases the intravascular display of homeostatic chemokines, and certain inflammatory chemokines which have been proposed to be classical HSPs based on their regulation by HSP transcription factors (Skitzki, Joseph J, et al. "Hyperthermia as an Immunotherapy Strategy for Cancer," Current opinion in investigational drugs (London, England: 2000) 10.6 (2009): 550-58).

SUMMARY OF THE INVENTION

The present invention is based on the finding that heat and heat-based treatments may be used to modulate, inhibit and/or prevent one or more of the processes that contribute to certain vascular and/or arterial complications.

The term 'vascular and/or arterial complications' may include, for example, diseases and conditions which affect the arteries and general vasculature. Diseases and/or conditions of this type may be generally classed as 'cardiovascular diseases and/or conditions'. For example, the term 'vascular and/or arterial complications' may embrace diseases, conditions and/or complications such as atherosclerosis, stenosis, restenosis, in-stent restenosis, vascular occlusion (through the presence of a plaque, clot or thrombus) and the like.

Thus, the apparatus, methods and uses described herein may find particular application in subjects suffering from, or susceptible and/or predisposed to cardiovascular diseases and/or conditions, including for example those suffering from, predisposed and/or susceptible to, atherosclerosis or diseases or conditions associated therewith.

In some cases, existing treatments (for example angioplasty and stent-based treatments) result in alternate, additional and/or further complications and/or adverse events (restenosis and the like); the technologies described herein may equally be applied to the treatment, prevention and modulation of all complications and/or conditions associated with any of these treatments.

By way of example, the effects and/or symptoms of an arterial/vascular complication (for example an occluded artery or vessel) can be treated with, for example, balloon angioplasty and/or stent type procedures (including procedures which use bare metal stents (BMS) and drug eluting stents (DES)). However, the benefits and relief obtained are often short lived and the treatment can lead to other complications such as restenosis. Restenosis is a common phenomenon and is essentially a re-occurrence of stenosis, the narrowing of a blood vessel leading to restricted blood flow. Thus, while a stent may be used to re-model or widen the lumen of a narrowed or occluded vessel restenosis is a frequent and frustrating side-effect.

Restenosis following the fitting of a stent is often referred to as in-stent restenosis (ISR). Restenosis following a balloon angioplasty procedure can be referred to as post-angioplasty restenosis (PARS).

As stated, procedures of this type either force the widening of the lumen of an occluded vessel or, in the case of balloon angioplasty used to treat atherosclerotic plaques, squashes or re-models the plaque to achieve widening and reduce the blockage. However, all of these procedures can result in irritation, damage or trauma to the vessel walls. This may, in turn, lead to some immediate effects including irritation, bleeding, thrombosis, clot formation and inappropriate (or inflammatory) immune responses. Any or all of these effects can lead to additional vessel narrowing or occlusion. Later, often sometime later, there may be a proliferation of smooth muscle cells (neointimal hyperplasia (NIHA)); again, this can lead to restenosis.

As such, the biological mechanisms which underpin many arterial and/or vascular complications (including stenosis, restenosis and/or in-stent restenosis) are varied and complicated; however, without wishing to be bound by theory, it is suggested that these complications may arise as a result of immune responses (including inflammatory and other cytokine/cell based responses), cell proliferation events (including growth of smooth muscle cells or neointima (proliferation of smooth muscle cells in the media layer), trauma (caused, for example, by some surgical procedure) and/or disease.

The present disclosure provides apparatus (or devices), methods and uses which may find application in the prevention, treatment and/or modulation of one or more of those events, processes and pathways that are associated with or which lead to or cause, arterial and/or vascular complications such as any form of restenosis. Nevertheless, it should be noted that the apparatus, methods and/or uses described herein may be applied to any form of peripheral arterial/vascular disease (PA/VD) and or related or associated conditions in other parts of the body (including for example those complications occurring in arteries and/or vessels in or proximal to organs such as the brain, kidney, liver and eyes). For example, the technology described herein can be exploited in the treatment and/or prevention of diseases and/or conditions, symptoms and/or effects associated with the same or complications arising from surgical intervention and/or treatment in one or more of the carotid, aorta, iliac, femoral, popliteal and tibial arteries.

The apparatus, methods and uses described herein may also be used to improve, enhance or supplement existing procedures for the treatment of cardiovascular diseases and/or conditions such as, for example, atherosclerosis. Thus, the apparatus, methods and uses may be exploited together, concurrently or in parallel with existing treatments and procedures.

The disclosure provides a method of treating or preventing an arterial and/or vascular complication, said method comprising applying a heat treatment to an arterial and/or vascular tissue of a subject in need thereof.

It should be noted that throughout this specification the term "comprising" is used to denote that embodiments of the invention "comprise" the noted features and as such, may also include other features. However, in the context of this invention, the term "comprising" may also encompass embodiments in which the invention "consists essentially of" the relevant features or "consists of" the relevant features.

The arterial and/or vascular complication may be any form of cardiovascular disease, peripheral arterial disease and/or peripheral vascular disease.

The arterial and/or vascular tissue may be a diseased and/or damaged arterial and/or vascular tissue.

The "arterial and/or vascular complication" may take the form of a disease and/or condition such as, for example atherosclerosis, stenosis and/or some complication or effect associated with an existing treatment for the same, including for example all forms of restenosis.

A subject in need thereof may be any human or animal subject suffering from or predisposed and/or susceptible to a vascular or arterial compilation. Thus, the subject may be suffering from a cardiovascular disease, atherosclerosis, some form of stenosis or arterial/vascular occlusion and/or is susceptible or predisposed to (or suspected of suffering from) the same. The subject may have undergone some form of surgical procedure to correct or treat some form of vascular and/or arterial complication. The subject may have been fitted with some form of stent. The surgical procedure may have taken place sometime before a method of this disclosure and/or may be conducted concurrently (or in combination or together with) one or more of the methods outlined herein. Alternatively, the surgical procedure may have been conducted after, for example immediately after, a method of this disclosure.

This disclosure provides a method of treating or preventing neointima and/or an associated proliferation of smooth muscle cells, said method comprising subjecting a blood vessel exhibiting or susceptible and/or predisposed to neointima, to heat at a temperature and for a period of time sufficient to treat or prevent the neointima and/or associated proliferation of smooth muscle cells. One of skill will appreciate that the proliferation and migration of smooth muscle cells in blood vessels can result in the thickening of the walls of the blood vessel (including arteries and the like) and decreased or reduced lumen space. By inhibiting or reducing neointima, it may be possible to reduce any subsequent vessel narrowing or obstructions which are associated therewith. The proliferation of smooth muscle cells within the layers of tissue around a vessel (and which can lead to narrowing of that vessel) may be referred to as neointimal hyperplasia.

As such, there is provided a method of treating, preventing, inhibiting and/or modulating neointimal hyperplasia, said method comprising subjecting a blood vessel exhibiting or susceptible and/or predisposed to neointimal hyperplasia, to heat at a temperature and for a period of time sufficient to treat, prevent, inhibit and/or modulate the neointimal hyperplasia.

It should be noted that throughout this application the term "modulate" is used to denote that the methods, apparatus and/or uses described herein have some effect upon certain vascular and/or arterial complications. The term "modulate" should be taken as meaning that the described method, uses and/or apparatus is capable of enhancing, stimulating and/or inhibiting said complication and/or any process or pathway associated therewith. Thus, for example, in the case of heat treatment-based methods which may be used to modulate neointimal hyperplasia, the method may inhibit, reduce or suppress neointimal hyperplasia and/or any processes or pathways associated therewith.

There is further provided a method of treating and/or preventing atherosclerosis and/or one or more symptoms, effects and/or complications associated therewith, said method comprising applying a heat treatment to an atherosclerotic tissue of a vessel. The term "atherosclerotic tissue" may embrace any area or part of a vessel that exhibits a symptom of atherosclerosis including, for example, an atheroma or atherosclerotic lesion/plaque. The term "atherosclerotic tissue" may include asymptomatic tissues located upstream or downstream of a site of atherosclerosis. The heat treatment may be applied at a temperature and for a time period suitable to treating and/or prevent atherosclerosis in a subject in need thereof.

A method of this invention may further be used to treat, prevent or modulate a form of stenosis or restenosis, said method comprising applying a heat treatment to an artery or vessel diagnosed as having stenosis or restenosis and/or which is susceptible and/or predisposed to the same. One of skill will appreciate that stenosis and/or restenosis may be detected and/or diagnosed in a variety of different ways including by, for example X-ray based procedures (for example CT scans and the like), ultrasound (as applied in echocardiogram type procedures), magnetic resonance imaging (MRI: optionally with contrast agents (magnetic resonance angiography)). It should be noted that the term "restenosis" as used herein embraces in-stent stenosis (ISR).

The heat treatment to be exploited may comprise application of heat at a temperature and for a duration suitable to treat or prevent the vascular and/or arterial complication.

The heat may be applied at a temperature of between about 30 Deg C. to about 60 Deg C. For example, the heat may be applied at a temperature of anywhere between about 43 Deg C. and about 50 Deg C. The heat may be applied at any temperature between any of these ranges, including (+/−0.5 Deg C.) at a temperature of about 31 Deg C., about 32 Deg C., about 33 Deg C., about 34 Deg C., about 35 Deg C., about 36 Deg C. 37 Deg C. 38 Deg C. 39 Deg C. 40 Deg C. 41 Deg C. 42 Deg C., about 43 Deg C., about 45 Deg C., about 46 Deg C., about 47 Deg C., about 48 Deg C., about 49 Deg C., about 50 Deg C., about 51 Deg C., about 52 Deg C., about 53 Deg C., about 54 Deg C., about 55 Deg C., about 56 Deg C., about 57 Deg C., about 58 Deg C., about 59 Deg C.

While the methods described herein may use a single specific temperature, the methods may alternatively use or exploit two or more different temperatures. Indeed, for the duration the heat is applied, the temperature may be varied from a first temperature to one or more other temperatures. For example, the method may comprise the delivery of two or more predetermined temperatures or may comprise a steady or regulated temperature rise between a first and second temperature.

The temperature may be applied for any suitable time including for anywhere between about 1 second (s) and 5 minutes (mins). For example, the selected temperature may be applied for anywhere between about 5 s, 10 s, 15 s, 20 s and 30 s to about 1 min, 2 min, 3 min or 4 min. The temperature may be applied for 10 s, 15 s, 20 s or 25 s or for longer at about 1 min, 1.5 min (90 s), 2 min, 2.5 min, 3 min (180 s), 3.5 min, 4 min or 4.5 min. In one embodiment, the selected heat may be applied for any period of time between about 15 s and about 180 s.

Microwave energy may be used to apply the heat treatments described herein.

Microwave energy for use according to this disclosure may have a frequency of between about 500 MHz and about 200 GHz. In other embodiments, the frequency of the microwave energy may range from between about 900 MHz and about 100 GHz. In particular, the frequency of the microwave energy may range from about 5 GHz to about 15 GHz and in a specific embodiment has a frequency of about 6 GHz, about 7 GHz, about 7.5 GHz, about 8 GHz, about 8.5 GHz (for example from about 7.5 GHz-about 8.5 GHz), about 9 GHz, about 10 GHz, about 11 GHz, about 12 GHz, about 13 GHz or about 14 GHz.

The microwave energy may be delivered at a power of anywhere between about 1 W and about 20 W. For example, the microwave energy may be delivered at a power of about 2 W, about 3 W, about 4 W, about 5 W, about 6 W, about 7 W, about 8 W, about 9 W, about 10 W, about 11 W, about 12 W, about 13 W, about 14 W, about 15 W, about 16 W, about 17 W, about 18 W or about 19 W. The microwave energy may be delivered at a single fixed power or at a range of different powers.

An advantage associated with the use of a microwave energy-based heat treatment is that it is rapid and precise and can even be used in combination with stents, including metallic stents with no negative shielding impact. It should be appreciated that different dimension of antenna parameter may suit different balloon sizes for optimal SAR or an optimal common design may be used. Further, the distribution of heat induced by microwave energy is better than as occurs using other (for example resistive coil based) methods—indeed the heat penetrates tissues quickly and with less thermal gradient—this avoids unwanted apoptosis and loss of cell viability. Nevertheless, the ability of microwave energy to effect a rapid and precise rise in temperature is beneficial in the clinical environment where time occluding an artery for example with the PTCA is preferred to be kept to a minimum (rapid and precise heating allowing the operator to spend less time conducting a procedure).

An important aspect of this disclosure is maintaining the temperature of the tissues as this helps achieve the correct biological response and subsequent clinical outcome. The inventors have shown through in-vitro experiments that low power microwave energy, for example energy delivered at about 5 W or less was sufficient to maintain a temperature in its surroundings for a period of time.

Figure 11A:
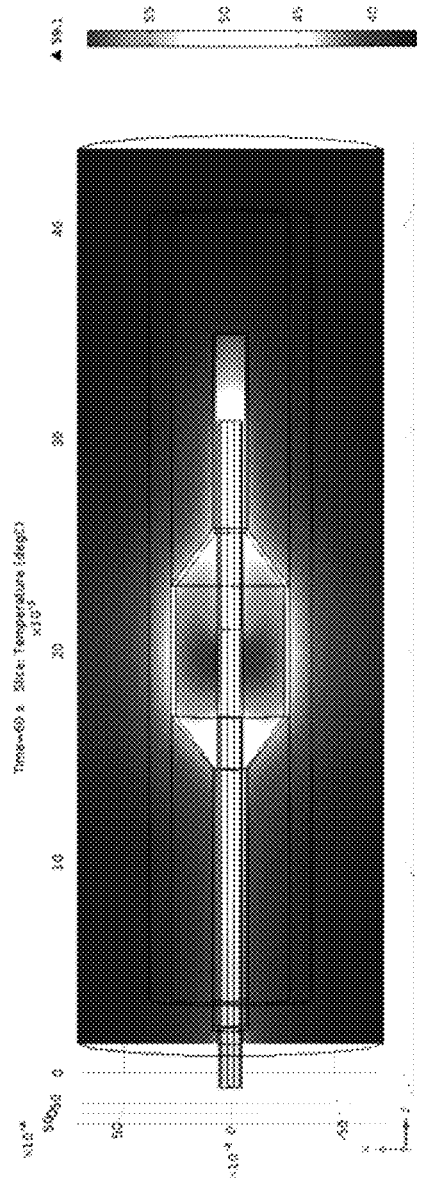

A comparison with non-microwave antenna-based heating such as heating using a resistive coil to heat fluid in the balloon, was made with a Comsol simulation model implementing a bioheating equation. FIG. 11A shows the poor distribution of heat into the vessel wall in comparison with FIG. 11B where the microwave antenna penetrates more quickly and with less thermal gradient that can lead to unwanted apoptosis The heat treatment may be applied directly or indirectly to the tissues of a vessel or artery or indirectly via a fluid—for example a fluid used to inflate the balloon element of a balloon catheter.

For example, the methods may exploit an apparatus comprising a microwave source (an antenna) for providing microwave energy and means for delivering the microwave energy to a subject or tissue (artery or other vessel) to be treated. Such an apparatus may be used in any of the therapeutic methods described herein.

An apparatus suitable for use in the methods described herein may further comprise means for controlling at least one property of the microwave energy produced by the microwave source. For example, the means may control or modulate the power, frequency, wavelength and/or amplitude of the microwave energy. The means for controlling the microwave energy may be integral with the apparatus or separately formed and connectable thereto.

The microwave energy source or antenna may be configured to produce precise amounts of microwave energy at a single frequency and/or microwave energy across a range of frequencies. The means for controlling at least one property of the microwave energy may permit the user to select or set a particular microwave or microwaves to be produced by the apparatus and/or the properties of the microwave(s) produced.

The apparatus may further comprise means for monitoring the microwave energy produced or generated by the microwave source. For example, the apparatus may include a display indicating one or more properties of the microwave energy.

The apparatus may further comprise a delivery catheter, a balloon catheter contained therein and a balloon in which the microwave source (or antenna) is housed.

Thus, the apparatus for use in any of the methods described herein may comprise a modified balloon catheter, wherein said modified balloon catheter comprises a microwave emitter—for example an antenna.

The apparatus (for example modified balloon catheter) may further comprise a pressure sensing system. An advantage associated with the incorporation of a pressure sensing system is that it assists in the selection of the correct energy to ensure delivery of the correct heat/dose into the cells and tissues which surround the antenna and/or apparatus.

Thus, this disclosure provides any of the apparatus described herein for use in the various described methods.

A heat treatment (for example a microwave energy-based heat treatment) may be applied at one or more points during a PTCA type procedure. For example, the heat treatment may be applied to the site of a vascular or arterial complication before, during and/or after any surgical procedures aimed at reducing or removing a vascular or arterial occlusion. For example, a standard PTCA procedure may include a pre-dilation step which occurs before any step delivering and deploying a stent to a particular site within a vessel or artery. Thus, a heat treatment, for example a microwave energy-based heat treatment, may be used at any point in such a process. A heat treatment may be applied continuously throughout a PTCA process or regularly and at pre-determined points. Each heat treatment application may comprise the same or different treatment parameters (temperature, time and the like). For example, a first heat treatment applied at some point during a PTCA process may be the same or different (in terms of temperature applied and duration of temperature exposure) for second and subsequent heat treatments applied at other points during the PTCA process.

As such, a heat treatment according to this disclosure (for example a microwave-based heat treatment may be applied pre- or post-intervention by or with a stent, a bare metal stent, a drug eluting stent, bioresorbable stent, plain old balloon angioplasty and drug eluting (or impregnating) balloon.

The initial pre-dilation of the stent site area is known to cause trauma to the vessel wall as it is stretched by the expanding balloon. The effect of this trauma can be reduced if during the pre-dilation step the vessel tissue (at the point of dilation) is subjected to a heat treatment as outlined in this disclosure. Additionally, or alternatively, a heat treatment of this disclosure may be applied after (for example immediately after or post) any dilation step and/or occurrence of any stretch associated trauma. Without wishing to be bound by theory, it is suggested that heat-based treatments, such as the microwave energy-based treatments described herein, may promote repair of the site expanded by the balloon and initiate the production of cell protective heat shock proteins.

Thus, standard PTCA protocols may be altered either to use a modified balloon catheter as described herein (in other words a balloon catheter comprising a microwave source/antenna) and or multiple different balloon catheters—some with and some without microwave antennas.

Further, in any PTCA protocol, a heat treatment step may be introduced at one or more points. For example (and as stated above) the pre-dilation step may comprise a heat treatment. In other embodiments, the heat treatment is omitted from the pre-dilation step but used after and before any stent is released and/or implanted.

It should be understood that in all of these methods, a heat treatment may be applied with the use of a modified balloon catheter of this invention—that is a balloon catheter comprising a microwave source/antenna. A modified balloon catheter according to this invention may be referred to as a 'microwave balloon' (MWB). Likewise, a standard balloon catheter may be referred to a 'plain balloon' (PB). The process of releasing and/or implanting a stent may be may be referred to as "stent release" (SR). Thus using this notation, the following provides some non-exhaustive examples of where in a PTCA sequence ("-" identifies a step in the procedure sequence) a method or device of this disclosure may be used:

1. Balloon predilation (by plain balloon, PB)—Microwave Balloon (MWB, this invention)—Stent implant/release
2. MWB—PB—SR
3. MWB—PB—MWB—SR
4. MWB—PB—MWB—SR—MWB It should be noted that in instances 2, 3 and 4, the same MWB may be used or a new device.

In practice, it may be expedient for a physician to use a MWB type device of this disclosure to perform any pre-dilation balloon step—this minimises the number of 'exchanges' down the catheter but depending on when the heat treatment is to be applied, the microwave source may be activated (when needed) and deactivated when not required.

Additionally, it may also be necessary to consider that any pre-conditioning of the vessel should be conducted in a manner which minimises trauma thereto. For example, the balloon element of any catheter device described herein (including a microwave catheter) may be expanded such that it meets the vessel walls but does not exert sufficient pressure to damage the surface. For example, during a dilation process when balloon pressure is used to enlarge the vessel lumen, this can lead to tissue damage within the vessel. To counter this, the balloon pressure may be maintained at a static value and the microwave antenna powered or activated in order to apply the necessary heat treatment.

After a stent has been released or implanted, the inflation pressure of any balloon catheter type device (including the modified devices described herein) may again be regulated and controlled such that it is sufficient to meet the vessel walls but not provide a vessel expansion outcome. In such cases a revised The PTCA sequence becomes thus (notation (MWB and SR are as above):

1. Pre-dilation using an MWB (no power); inflation is maintained and then MWB is powered and conditioning is delivered for a time period—MWB deflated—SR
2. MWB (on, low pressure)—MWB (off, high pressure)—SR 3. MWB (on, low pressure)—MWB (off, high pressure)—MWB (on, high pressure)—SR
4. MWB (on, low pressure)—MWB (off, high pressure)—MWB (on, high pressure)—SR—MWB (on, low pressure)

As stated ISR is predominantly seen after stent (for example bare metal stent (BMS)) implantation (although the various methods and devices described herein may also be used with any other type of stent material). In order to rebalance the endothelial and smooth muscle wall cell environment, hyperthermia (HT: or heat treatment as described herein) may be implemented.

Forceful expansion of restenosis material back into a vessel wall may be carried out in the same manner as a PTCA—for example by using a plain balloon. This trauma can be treated before, after or before and after. Subsequent drug delivery via a drug eluting balloon (DEB) may be carried out as part of standard of care for ISR. In some circumstances an additional stent will be deployed into the ISR region, overlaying the original stent, using the same PTCA sequence as the de novo stent procedure.

The following non-limiting examples illustrate permutations where in a PTCA sequence for ISR, a heat treatment (or device) according to the disclosure may be used:
1. Plain Balloon expansion (PB)—Microwave Balloon (MWB, this invention)
2. MWB—PB
3. MWB—PB—MWB*
4. PB—MWB—DEB
5. MWB—PB—DEB
6. MWB—PB—MWB*—DEB
*new or re-use in the same patient possible As with the standard stent implementation options, a modified balloon catheter device according to this disclosure (i.e. a balloon catheter comprising a microwave source) may be used like a standard (or plain) balloon catheter insofar as the expansion operation (with the balloon component inflated and under high pressure) may be performed with the microwave source/antenna powered on or off. With such an arrangement, an alternative PTCA sequence becomes thus (note, the term "off" and "on" refer to the status of the microwave source/antenna):
1. MWB (off, high pressure)—MWB (on, high pressure)
2. MWB (on, low pressure)—MWB (off, high pressure)
3. MWB (on, low pressure)—MWB (on, high pressure)
4. MWB (off, high pressure)—MWB (on, high pressure)—DEB
5. MWB (on, low pressure)—MWB (off, high pressure)—DEB
6. MWB (on, low pressure)—MWB (on, high pressure)—DEB A particular advantage of the technology described herein over prior art devices and methods of treatment is that the induced hyperthermia (HT: or heat treatment) effects may offer treatment of an atheroma in isolation of any physical implants where the lumen loss does not warrant a stent. A treatment according to this disclosure may be used in lesions where the reversal or stabilisation of a plaque (atheroma) is needed. Without wishing to be bound by theory, the immune response cascade induced by a device of this disclosure and/or (a microwave based) heat treatment may lead to recruitment of 'fresh' macrophages that can remove the foam cells, reinitiating the efferocytosis process and allowing the equilibrium return to the immune cycle.

Enhancements to this resetting of atheroma environment may be intensified in conjunction with drugs delivered systemically or locally. These pharmaceutical ingredients may be activated by the elevated temperature caused by the heat treatment. Alternatively; the heat treatment activates pathways that the pharmaceutical ingredients act upon.

The implementation of atheroma treatment allows the same PTCA route as that used for treating or preventing ISR with or without a drug eluting balloon (DEB) loaded with pharmaceutical ingredients for the purpose of delivering a combination therapy to the atheroma rather than the cell wall of the lumen as traditionally delivered by a DEB. For clarification, a balloon with surface loaded with drugs intended to act on the atheroma may otherwise be referred to as a drug impregnating balloon (DIB) as the drug is intended to impregnate the cell walls and travel into the atheroma. If expansion of the balloon is needed to increase the cross-section or volume of the lumen then the present disclosure (and the apparatus and methods described herein) permit the use of a heat treatment (which has the benefit of inducing protective and healing properties); in such cases and using an apparatus or device of this invention, the following PTCA sequences are possible:
1. MWB (off, high pressure)—MWB (on, high pressure)
2. MWB (on, low pressure)—MWB (off, high pressure)
3. MWB (on, low pressure)—MWB (on, high pressure)
4. MWB (off, high pressure)—DIB—MWB (on, high pressure)
5. DIB—MWB (on, low pressure)—MWB (off, high pressure)
6. DIB—MWB (on, low pressure)—MWB (on, high pressure)

Without wishing to be bound by theory, the microwave energy induces a temperature rise at an inside surface of an artery or vessel (in other words in a surface adjacent the point at which the microwave energy is applied). The temperature rise may be localised and/or may spread away from the direct area to which it is applied and/or through the structural layers of the artery or vessel and/or into surrounding tissues, matrix and or structures. For example, where the vessel is an artery, the temperature rise associated with the (microwave based) heat treatment may be localised to the endothelial layer (that is the inner (inside) layer of the artery structure and/or any disease or complication associated structures (plaques, deposits, lesions or the like). While the temperature rise may be confined to the endothelial layer, it may spread from the exact site at which the heat treatment is applied. Further the energy applied may penetrate other structural layers to ensure that any temperature rise associated with the heat treatment, penetrates one or more of these other layers. For example, the energy (for example microwave energy) used to induce a temperature rise may be applied at a power and for a length of time sufficient to ensure that the temperature of not only the immediate endothelial layer (the 'tunica intima' layer) rises, but also all or part of the internal elastic lamina, the basement membrane, the smooth muscle (tunica media), the external elastic lamina and the fibrous connective tissue of the adventitia layer (tunica adventitia). Where the vessel is a vein, the energy (for example microwave energy) used to induce a temperature rise may be applied at a power and for a length of time sufficient to ensure that the temperature of not only the immediate endothelial layer (the 'tunica intima' layer) rises, but also all or part of the other layers and structures that make up the vein.

One of skill will appreciate that the exact parameters of the temperature rise (for example the magnitude of the rise) and the extent of its spread and penetration will depend on time and energy at (or for) which the microwave energy is applied.

The apparatus may further comprise means for controlling at least one property of the microwave energy produced by the microwave source. For example, the means may control or modulate the power, frequency, wavelength and/or amplitude of the microwave energy. The means for controlling the microwave energy may be integral with the apparatus or separately formed and connectable thereto.

In one embodiment, the microwave energy source may produce microwave energy at a single frequency and/or microwave energy across a range of frequencies. The means for controlling at least one property of the microwave energy may permit the user to select or set a particular microwave or microwaves to be produced by the apparatus and/or the properties of the microwave(s) produced.

The apparatus may further comprise means for monitoring the microwave energy produced or generated by the microwave source. For example, the apparatus may include a display indicating one or more properties of the microwave energy.

The microwave energy may be applied (using an apparatus described herein) may induce only a localised rise in temperature—the locality being confined to a particular tissue site—for example the site of some vascular or arterial complication. The temperature elevation may be localised to the surface of the skin and/or to the epidermal, dermal and/or sub-dermal layers thereof (including all minor layers that lie within).

Thus the disclosure provides a method of treating or preventing an arterial and/or vascular complication, said method comprising applying a heat treatment to an arterial and/or vascular tissue of a subject in need thereof, wherein the heat treatment comprises the application of heat at a temperature of between about 30 Deg C. and about 60 Deg C. for anywhere between about 1 second and 5 minutes.

The heat treatment may be delivered passively using processes and techniques which comprise applying heat to a tissue (for example an arterial and/or vascular tissue) through energy dissipation. Furthermore, HT can be classified into whole body HT, surface HT, loco-regional HT, perfusion HT and interstitial HT (Celsius, 2017). The primary effects of HT on human body centre on the innate and adaptive immune systems.

Without wishing to be bound by theory, it is suggested that heat treatment, including any microwave energy induced heat treatment induces a number of biological processes and pathways. These processes and pathways may be protective and/or healing. For example, the application of heat to arterial and/or vascular tissues may induce the production of heat shock proteins (HSPs), have an immunostimulatory effect and/or may suppress cell (for example (aberrant or inappropriate) smooth muscle cell) proliferation.

A heat treatment which induces the production of heat shock proteins may be beneficial for the treatment and/or prevention (or modulation) of certain arterial and/or vascular diseases and/or conditions. Heat shock proteins (HSPs) are produced in response to various cellular/tissue stresses and/or damage resulting from physical or environmental influences. Heat shock proteins are a class of functionally related proteins whose expression is increased when cells are exposed to elevated temperatures or other stress. As such, the methods of this disclosure, which methods exploit a heat-based treatment, may induce the production of heat shock proteins in arterial and/or vascular tissues. It is suggested (again without wishing to be bound by theory) that induction of HSP in the tissues, cells and media that surround damaged or diseased arteries and/or vessels, is a means by which some of the damage induced by the arterial and/or vascular complications described herein can be treated, prevented and/or modulated (inhibited and/or suppressed).

Activation of a HSP response via any of the heat treatments described herein may also induce aspects of the host immune response. For example, HSP may be involved in immunological stimulation and can be both pro- and anti-inflammatory depending on the pathway followed, e.g. adaptive or innate immune response. Thus, by inducing the expression of HSPS, the heat treatments described herein may further modulate local immune responses (in other words immune responses within the vascular and/or arterial tissues immediately surrounding the site of heat treatment) which are either pro- or anti-inflammatory—this promotes healing and reduces the effects of PTCA induced trauma and the occurrence of stenosis or restenosis.

Other effects associated with the application of (microwave based) heat treatment as outlined herein include, for example, reduced macrophage infiltration and/or recruitment following surgical intervention and/or a PTCA type procedure. One of skill will appreciate that macrophage infiltration may lead to inflammation and/or other immunopathologies and as such exploiting the heat treatment-based methods described herein may help reduce or suppress this phenomenon and lead to lower instances of restenosis.

It is also noted that when tissues and/or cells are exposed to temperatures of around 40 Deg C., there is enhanced migration of dendritic cells which assist in the drainage of lymph nodes, promote lymphocytes trafficking to lymphoid and tumour tissue and regulate lymphocyte survival and persistence in peripheral tissues by deregulation of c-FLIP. Without wishing to be bound by theory, it is suggested that heat treatments of the type described herein (which induce production of heat shock proteins and activate other biological systems and pathways) may help modulate the migration of lymph nodes to atheroma regions and/or the formation of mini-nodes within atheroma regions. In other words, the heat-based treatments described herein may be used to reset, enhance and/or improve the local lymphatic response that supports an atheroma or plaque.

An additional affect associated with the application of heat to vascular and arterial tissues is the priming of cells for the systemic and/or localised administration of drugs—perhaps via a drug eluting stent or balloon. This 'priming' effect is based on two observations. Firstly, CT for tumours is more effective with hyperthermia (an atheroma may be used as a surrogate for the tumour and CT scenario). Thus, a certain elevated temperature may begin to damage cells that are then more easily overcome/treated by some pharmacological agents (including those used in drug eluting stents and balloons). As such, the heat treatment-based methods of this invention may be used not only to treat or prevent vascular and/or arterial complications but to render the cells and tissues of an artery or vessel (including any diseased cells or tissues) more susceptible to the drugs used in eluting stents and balloons.

Thus, the methods and apparatus (devices) of this invention may be exploited as a means to induce the production of heat shock proteins in and around arterial and/or vascular tissues. As stated, heat shock proteins may have a protective and/or healing effect and so their production may help treat, prevent and/or modulate some of the damage and stress imparted by standard treatments for vascular and/or arterial complications as detailed above.

In addition to the above, the disclosure provides the use of heat treatment for treating or preventing any of the vascular and/or arterial complications described herein. Further, the disclosure provides the use of microwave energy for treating or preventing any of the vascular and/or arterial complications described herein. It should be noted that while the disclosure has predominantly been described with reference to a method of treatment and an apparatus or device, the definitions and descriptions apply equally to these uses.

The disclosure further provides kits for treating and/or preventing vascular and/or arterial complications, said kits comprising a modified balloon device described herein and instructions for use. The kits may comprise a system as shown in FIG. 1 and may further optionally comprise reagents including contrast reagents to assist in angioplasty procedures.

DETAILED DESCRIPTION OF THE INVENTION

The present invention will now be described in detail with reference to the following figures which show:

FIG. 1: A diagram showing a microwave power generator and balloon antenna system.

Figure 2:
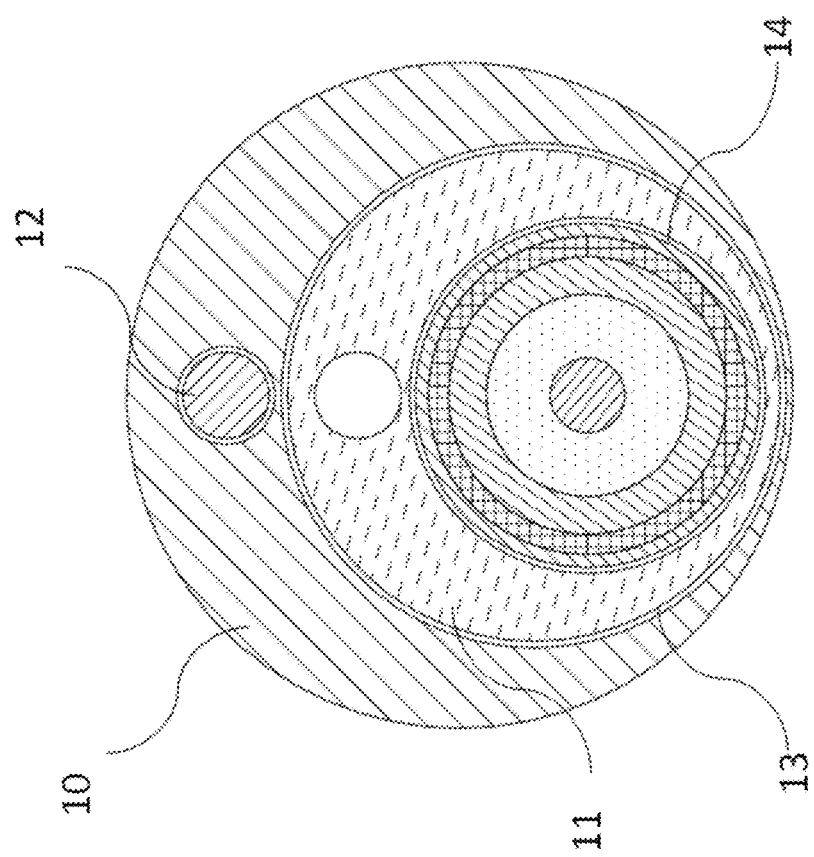

FIG. 2: A cross section through a percutaneous transluminal coronary angioplasty device.

Figure 3A:
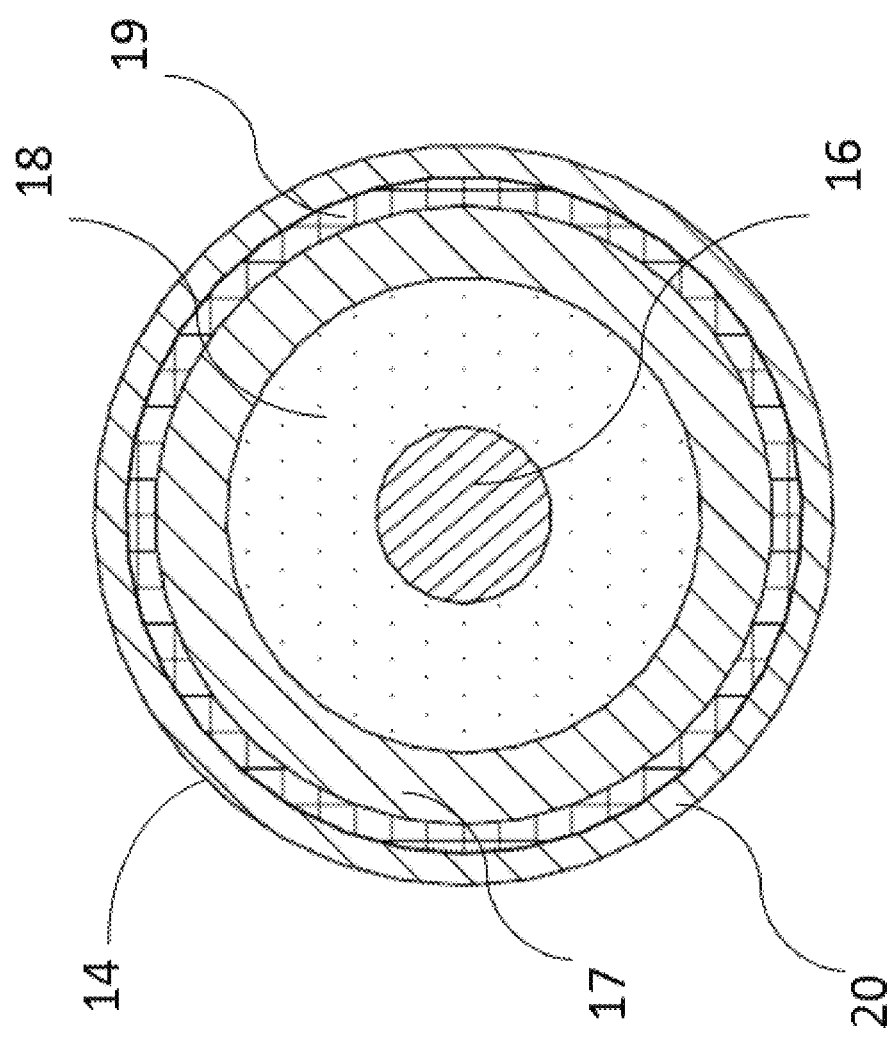
Figure 3B:
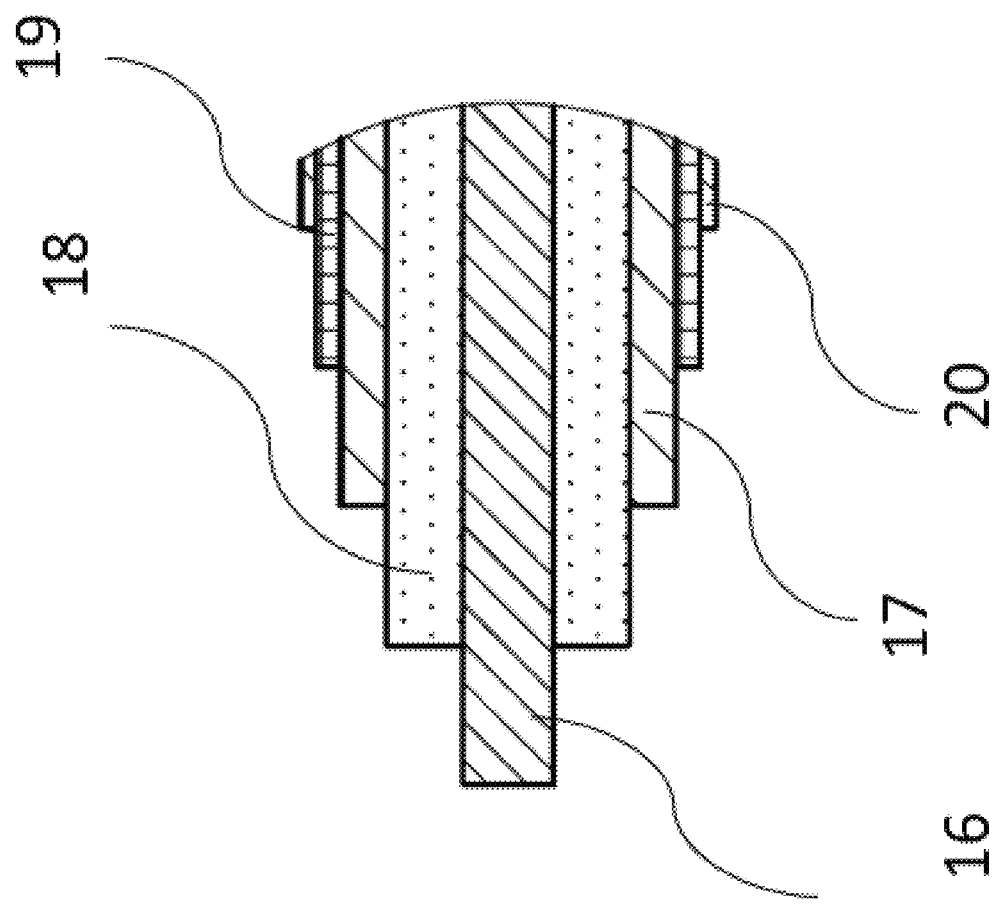

FIGS. 3A and 3B: FIG. 3A shows a cross-sectional view of a typical coaxial transmission line.

Figure 4:
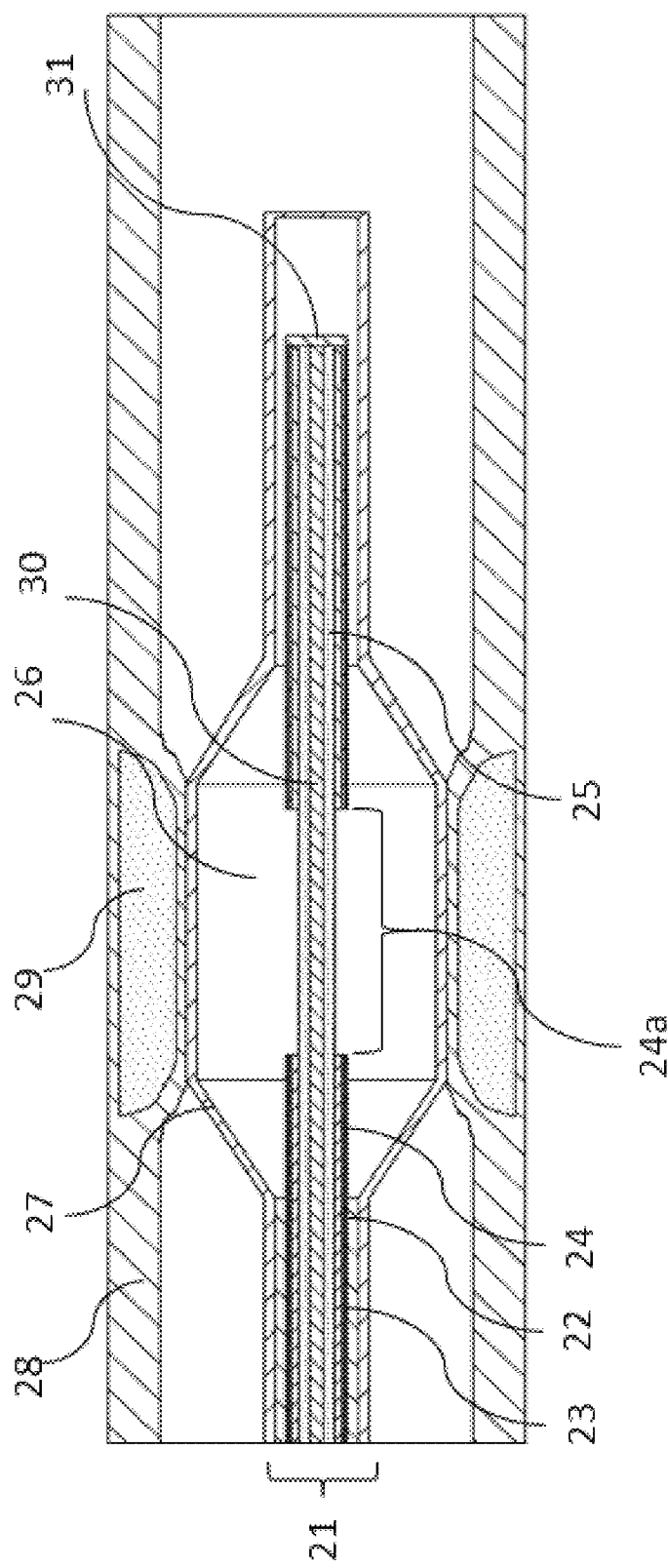

FIG. 4: Longitudinal section through a microwave balloon catheter device according to this disclosure.

Figure 5:
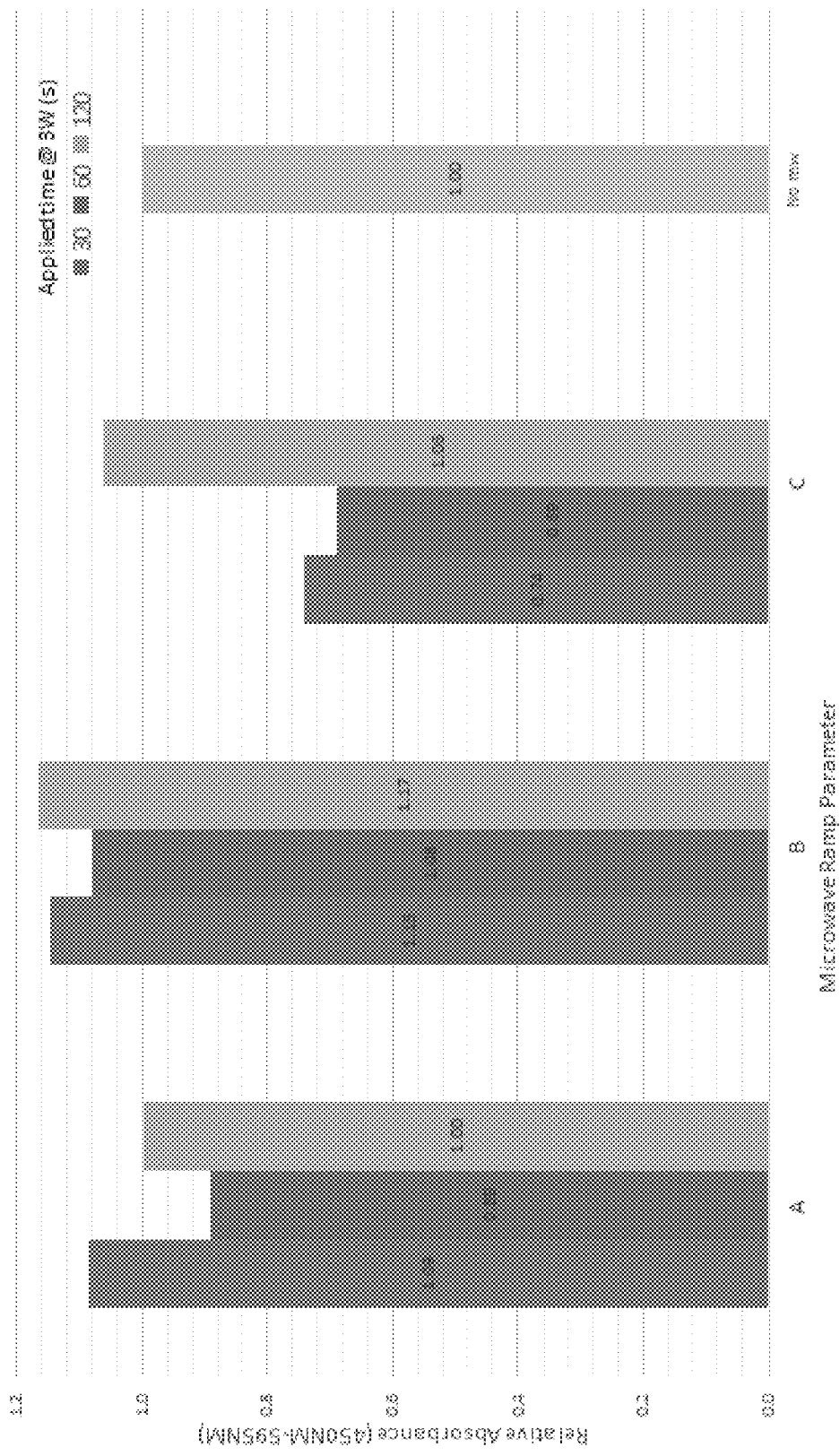

FIG. 5: HUVEC—ATP viability analysis post microwave treatment.

Figure 6:
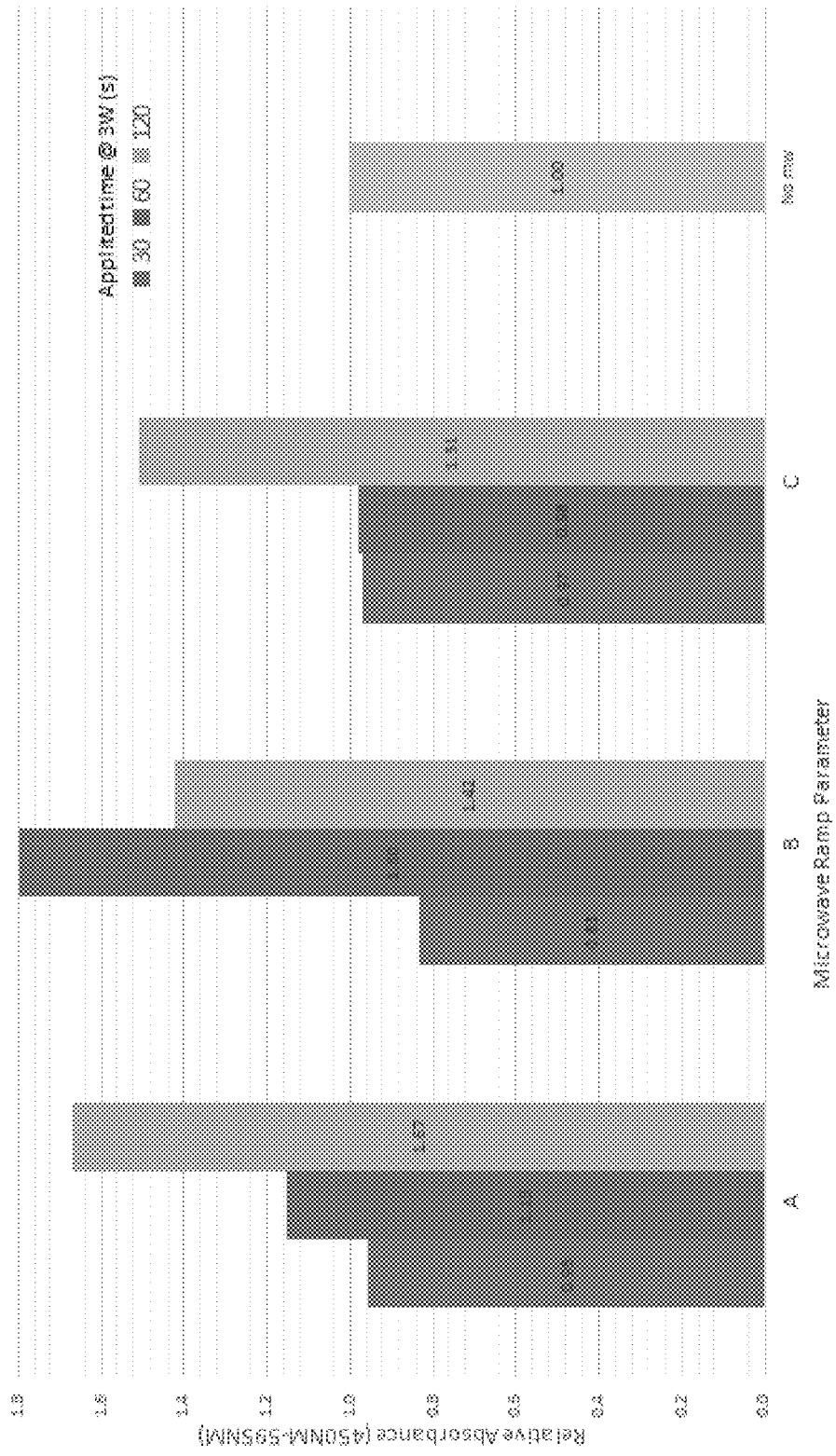

FIG. 6: VMSCs—ATP viability analysis post microwave treatment.

Figure 7:
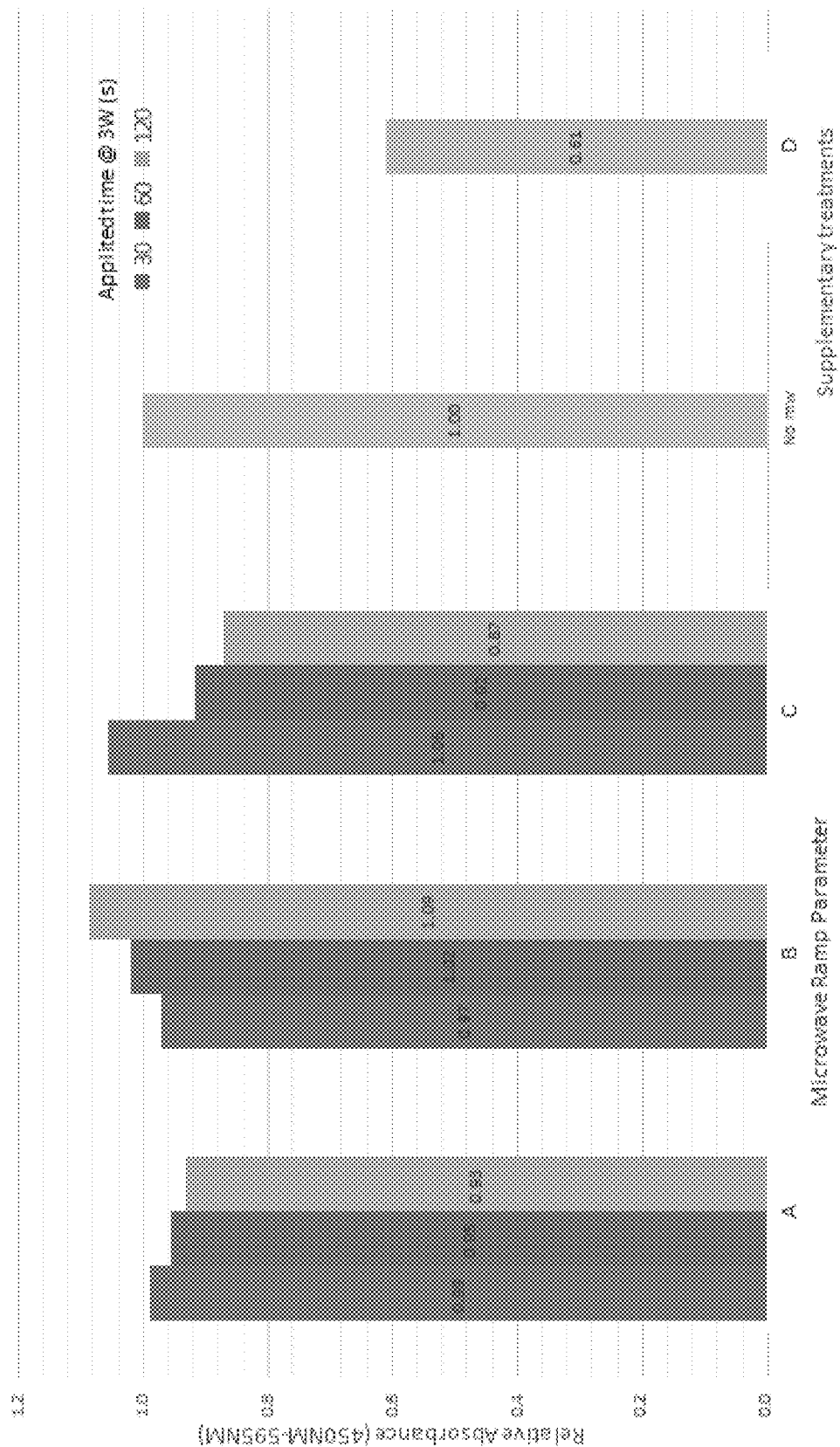

FIG. 7: VSMC—BrdU proliferation analysis post microwave treatment.

Figure 8:
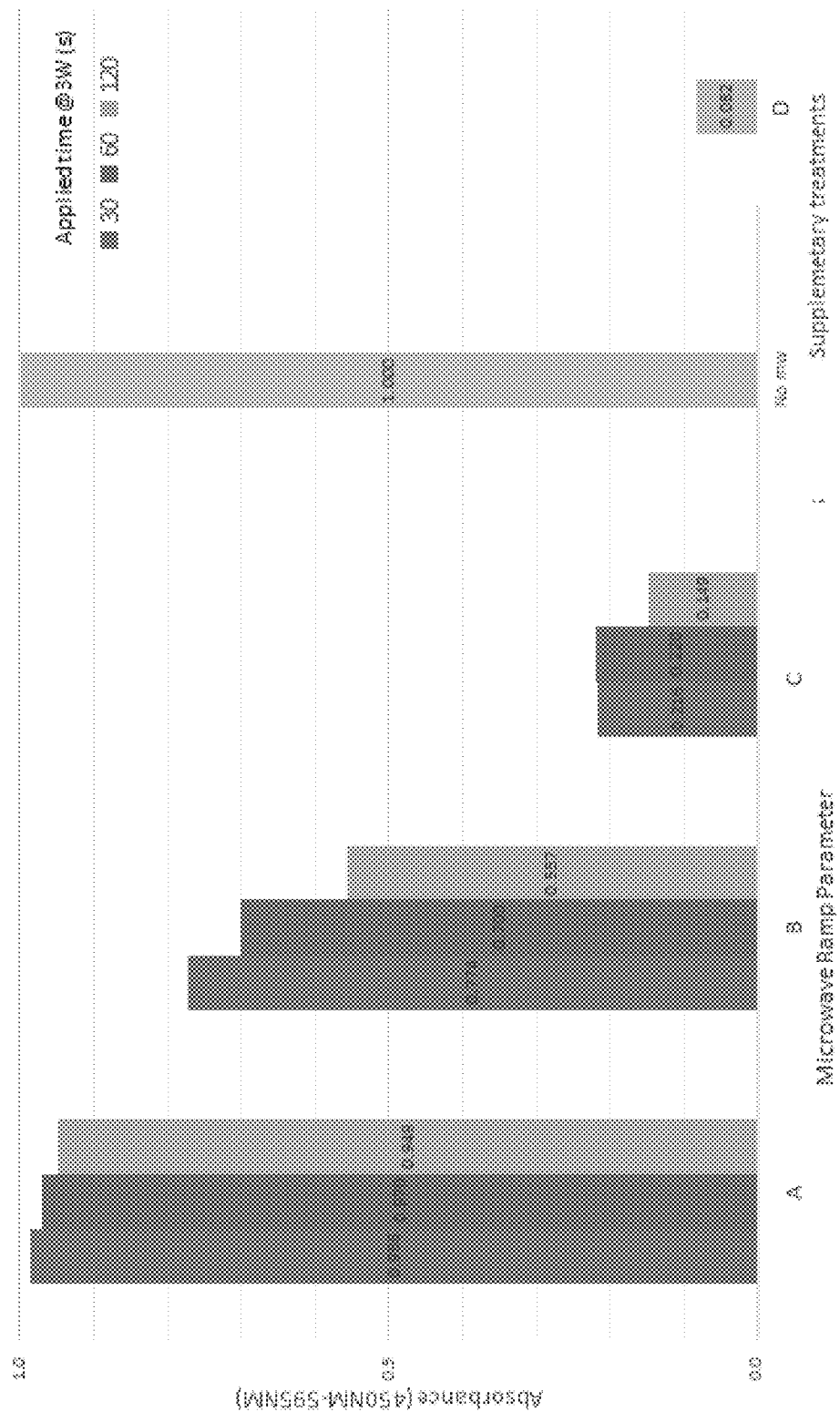

FIG. 8: Macrophages—BrdU proliferation analysis post microwave.

Figure 9A:
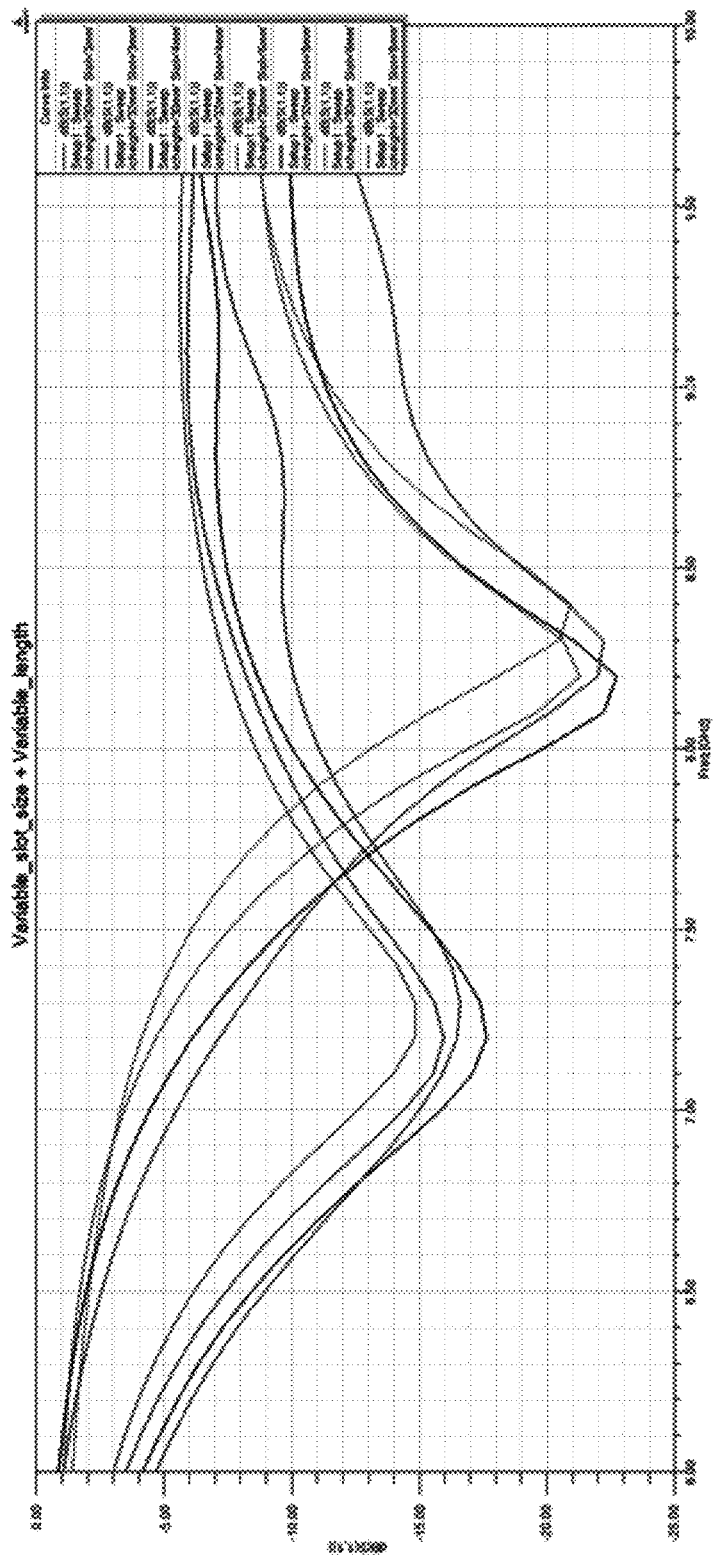
Figure 9B:
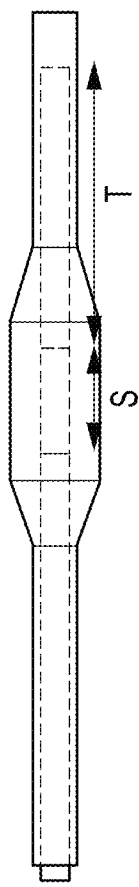

FIGS. 9A and 9B: FIG. 9A is a plot showing return loss against frequency for a set of lengths; FIG. 9B shows monopole dimension parameters S and T.

Figure 10A:
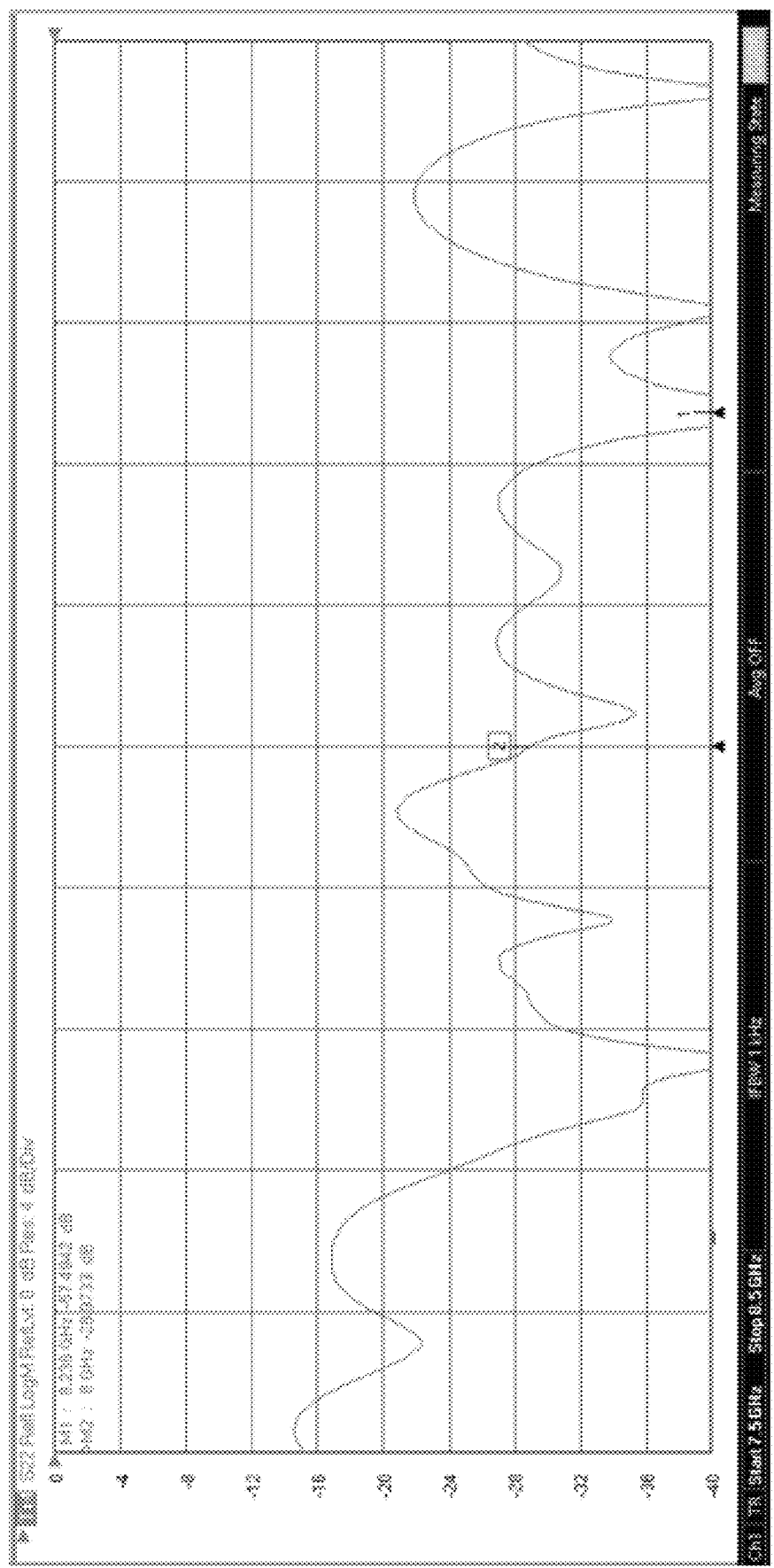

FIGS. 10A, 10B, and 10C: FIG. 10A is a plot of the return loss Sll in decibels against frequency in GHz over a range from 7.5 GHz to 8.5 GHz. FIG. 10B is a specific absorption rate (SAR) plot of side view representation of the antenna, inflated balloon with saline and iohexol 300 (1:1) in a vessel embedded in muscle. FIG. 10C shows specific absorption rate (SAR) plot showing the impact of a metallic stent.

Figure 11B:
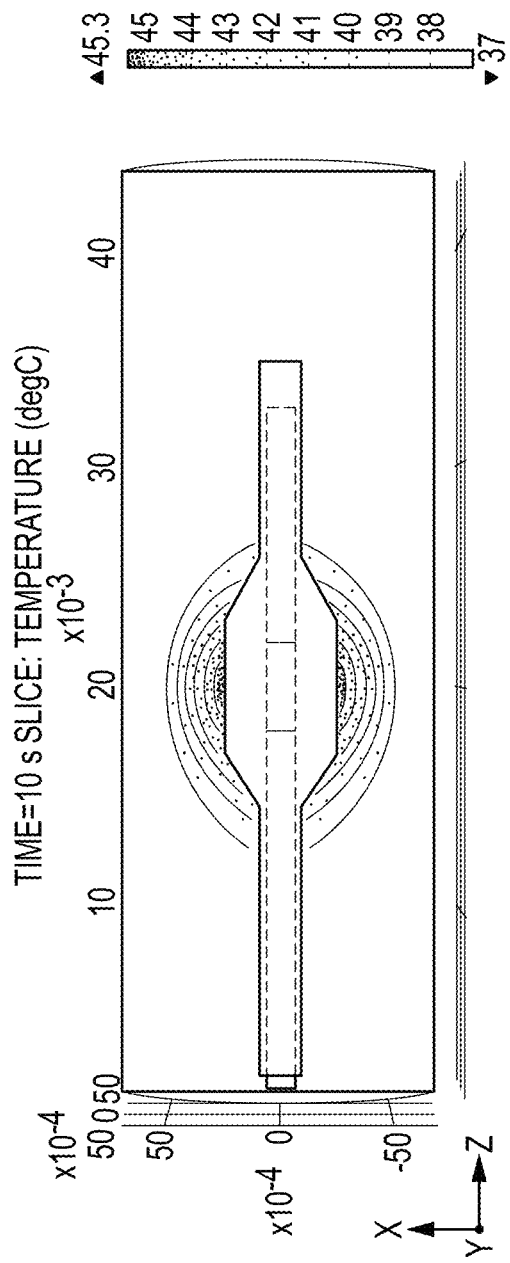

FIGS. 11A and 11B: Comsol simulation model implementing a bioheating equation to compare non-microwave antenna-based heating such as heating using a resistive coil to heat fluid in the balloon. FIG. 11A shows distribution of resistive coil induced heat into the vessel wall, in comparison with FIG. 11B, which shows microwave antenna induced heat.

Figure 12:
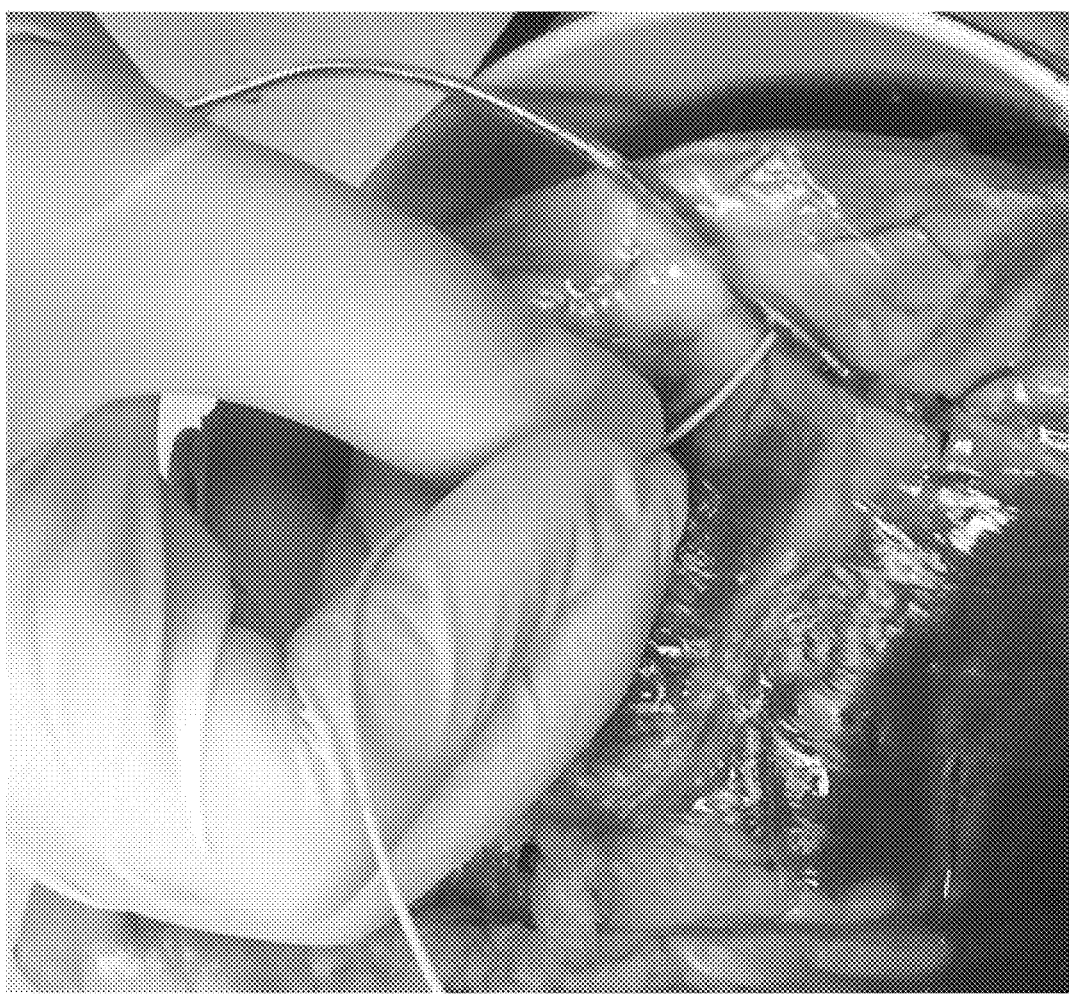

FIG. 12: photo of a prototype being tested in an excised bovine heart.

Figure 13:
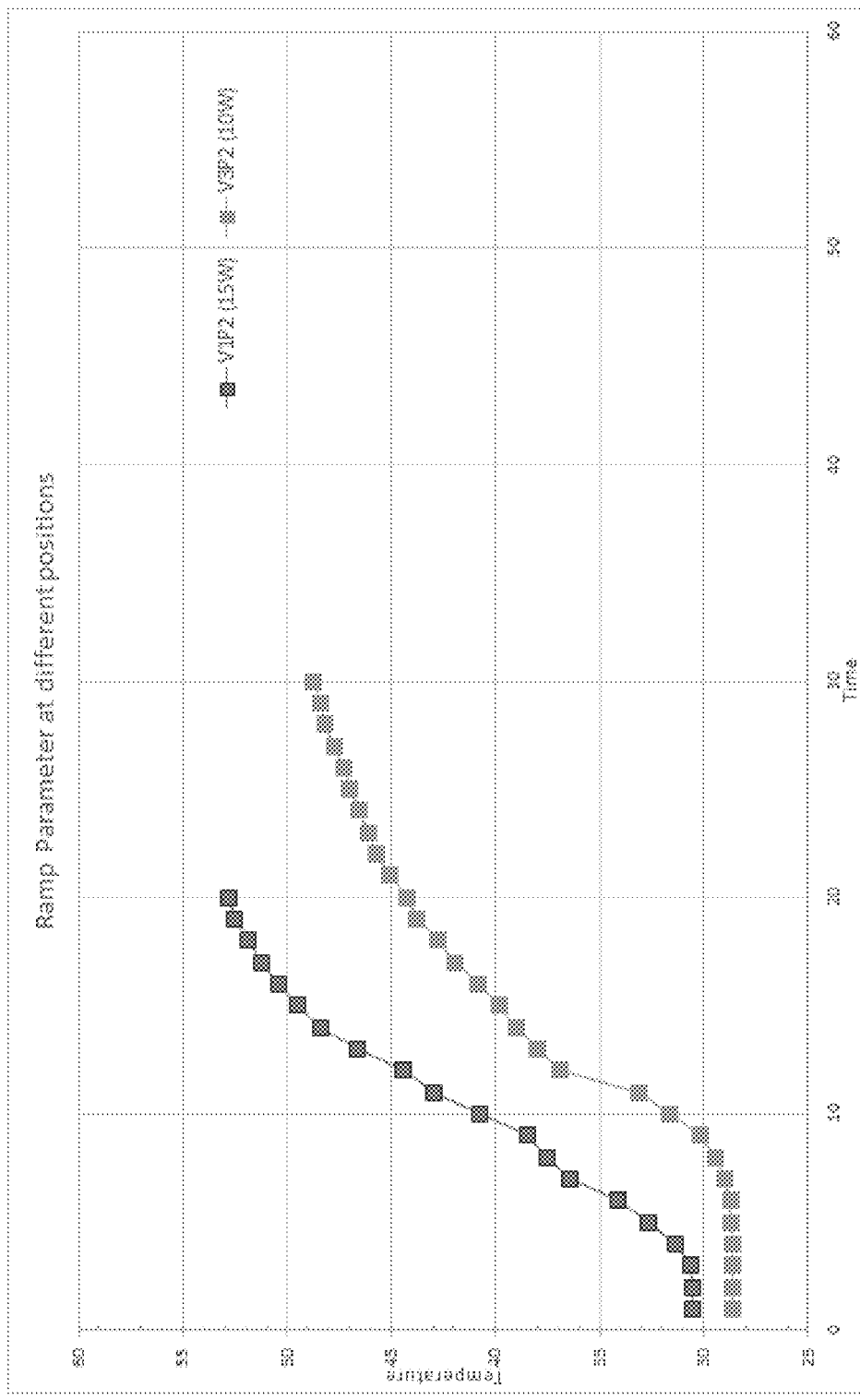

FIG. 13: Ramp parameter at different positions.

Figure 14:
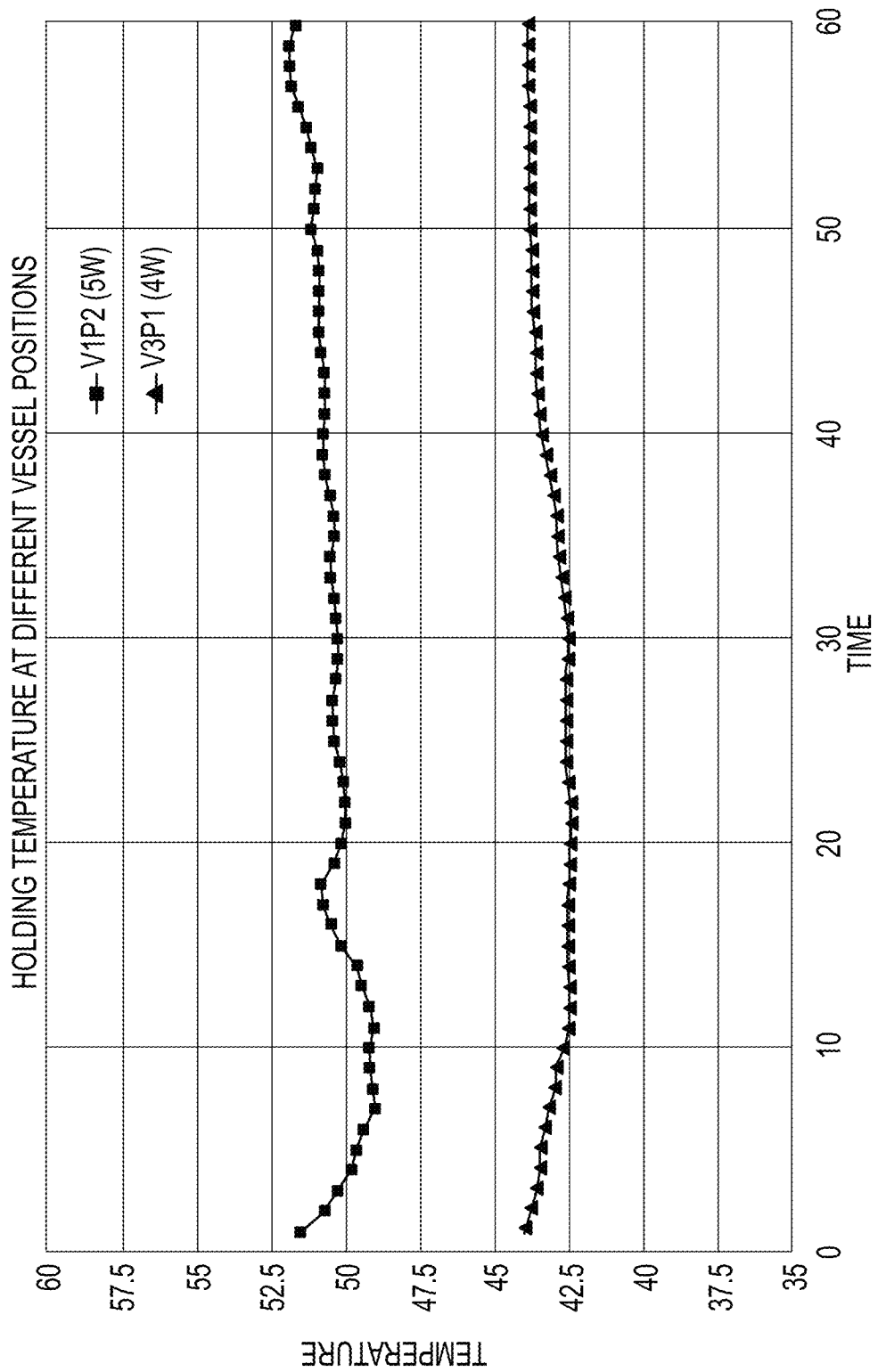

FIG. 14: Holding temperature at different vessel positions.

As shown in FIG. 1, the system comprises a microwave source 1 for providing microwave energy. The source 1 is connected to a system controller 2 which allows a user to control at least one property of the microwave radiation provided by the source 1. For example, system controller 2 may allow the user to modulate the power, frequency, wavelength and/or amplitude of the microwave energy. The system further comprises a reflection monitoring system 3 for monitoring the delivery of energy and a series of interconnects (or transmission lines 4, 5) which feed into a balloon catheter device which in this figure comprises a delivery catheter 6, a balloon catheter contained therein 7 and a balloon 8 in which antenna 9 is housed. Connected to balloon catheter 7 is a pressure sensing system 20 which can be used to monitor, control and regulate the inflation (and pressure) of the balloon component 8. The antenna 9 is configured to deliver precise amounts of microwave energy provided by source 1 at a single frequency or across a range of frequencies.

FIG. 2 shows a cross section of a percutaneous transluminal coronary angioplasty device according to this disclosure. As stated, useful devices may be modified so as to comprise a microwave source and an antenna for delivery of the same. In this figure the device is shown to comprise 3 basic elements: a flexible guiding catheter 10, the flexible balloon catheter 11 and the flexible guidewire 12. The guidewire is first inserted and steered into the target vessel by the operator using X-ray imaging. In the case of the monorail or rapid exchange configuration as it is known, a dual lumen catheter is delivered along the guidewire. The guiding catheter section contains the balloon catheter assembly 13 which in addition contains a large second lumen both housing the transmission line (coax) 14 and inflation liquid to coexist in the channel. Additionally, there may be two further lumens beyond the guidewire lumen, in order to house the transmission line (coax) and inflation liquid independently.

The materials used to form catheters 10 and 11 are typically biocompatible materials as they are to be used inside the vessels of a patient. Suitable biocompatible materials include, but are not limited to, medical grade thermoplastic elastomers made of flexible polyether and rigid polyamide fluoropolymers, polyolefins, polyurethane, polyethylene, or polyvinylidene fluoride or composites of these materials.

The construction of a typical transmission line (coax) shown in FIGS. 3A and 3B includes a flexible coaxial transmission line (coax) 14 including a flexible centre conductor 16 coaxial with a flexible cylindrical outer conductor 17. An insulating or dielectric material 18 fills the space between the centre conductor 16 and outer conductor 17 for holding the centre conductor 16 and outer conductor 17 in place and for electrically isolating the conductors from each other. The outer conductor 17 may be augmented with a second flexible conductive sheath or braid 19 which in these figures is further coated over its length by flexible jacket 20 made of an inert impermeable and low friction material such as FEP (Fluorinated ethylene propylene). A suitable type of coaxial transmission line is manufactured by HUBER+SUHNER (Switzerland) reference by type SUCOFORM_43_FEP_MED having nominal outer diameter of 1.09 mm.

In FIG. 4, the antenna component is integral to the flexible coaxial transmission line (coax) 21. The manufacture of the monopole antenna is made by the removal of the flexible jacket 22, the outer sheath 23 (if present) and the outer conductor 24 over a predetermined length and offset from the distal end of the transmission line (see feature 24a: antenna/emission section). The centre conductor 30 is electrically connected to the outer conductor 24 and outer sheath 23 the distal end of the transmission line 31. The insulating or dielectric material 25 is then exposed circumferentially, allowing the emission of the microwave energy. This arrangement produces a uniform electric field around the monopole antenna, coupling into the surrounding fluid 26 inflating the balloon 27, into the vessel wall 28 and atheroma 29. The balloon is bonded and sealed around the balloon catheter such that the position of the radiating element is optimally placed along the catheter axis, collinear to the balloon major axis.

Results

In-stent restenosis following percutaneous transluminal coronary angioplasty (PTCA) procedures such as balloon angioplasty and stenting occurs when the normally quiescent cells within the artery wall proliferate excessively in response to balloon injury or stent implantation.

Effect of Microwave Energy on Cell Viability and Proliferation

Experiments were conducted using cultured endothelial cells—specifically Human Umbilical Vein Cells (HUVECs) and vascular smooth muscle cells (VMSCs).

The cells were exposed to microwave heating using different powers and durations to assess the effect on cell viability. The cells were cultured and maintained at 37 C prior to and post microwave exposure and held in a 48 microwell plate with flat bottomed wells.

The Microwave energy was delivered from the underside of the plate in 2 stages, the first to ramp the temperature from 37 C to 3 therapeutic temperature zones under examination, referred to as A, B and C, equating to 42, 26 and 48 C cell temperatures. Each ramp condition used 15 W of power but for durations of 20, 30 and 40 s corresponding to A, B and C.

The second stage used a common fixed power of 3 W for 30, 60 and 120 s to observe the impact of time held at the elevated temperature. The viability of the cells after the various microwave conditions was assessed using standard protocols (including, for example, protocols which use a ViaLight+ (Lonza, Switzerland) assay kit, intended for the detection of cytotoxicity of mammalian cells and cell lines in culture by determination of their ATP levels). One of skill will appreciate that the measurement of ATP is the most accurate, effective, and direct way of determining the number of living cells in culture.

The data presented in FIGS. 5 and 6 shows that there is no detrimental effect to HUVECs and VMSCs and no apoptosis was detected. This suggests that neither the microwave frequency, power nor duration adversely affect the viability of HUVECs and VMSCs.

To assess the effect on cell proliferation the same microwave ramp conditions A, B & C with subsequent power of 3 W for 30, 60 and 120 s were repeated on the VSMCs and macrophage cells of type J744. The ability of cells to proliferate reflects on how adapted the cells are to their environment.

Cell proliferation was measured using a BrdU (bromodeoxyuridine) assay kit (Calbiochem).

Cells were seeded in 48-flat bottomed well plates and quiesced in 0.1% (v/v) FCS-containing medium for 24 h prior to treatment. Post treatment the VSMCs and macrophages were stimulated with 10% FCS-containing medium and addition of BrdU. The assay was performed as per the manufacturer's instructions and proliferation was detected using a spectrophotometric measurement of absorbance at dual wavelengths.

The results are shown in FIG. 7; there was a negligible effect on the VSMCs proliferation with parameters A, B, and C at varying hold durations.

A microwave power of 20 W was administered for 120 s in case D highlighting that higher microwave power can impair the proliferation of VSMCs. The detrimental effect of increased duration and power on macrophages is shown in FIG. 8.

Antenna Design

The optimisation of the antenna design used HFSS (Ansoft Corp, PA USA) modelling software which is a Finite Element Method (FEM) based full wave electromagnetic solver.

The monopole dimension parameters S and T, shown in FIG. 9B, were varied in relation to the placement in the balloon, an example of a plot showing return loss against frequency for a set of lengths is shown in FIG. 9A. Modelled return loss S11 in decibels is plotted against frequency in GHz over a range from 6 GHz to 10 GHz. The material parameters represent the properties inherent in the materials detailed in the description section with the addition of a liquid made at 1:1 ratio of saline water and contrast agent common in PTCAs (iohexol 300 mgI/mL: also known as Omnipaque 300, GE healthcare AS, Norway).

A manufactured prototype with the optimal parameters derived from the HFSS analysis was connected to a vector network analyser (VNA) to measure the return loss S11.

FIG. 10A plots the return loss Sll in decibels against frequency in GHz over a range from 7.5 GHz to 8.5 GHz. The operation of one embodiment of system uses 8 GHz for which the antenna tested exhibits sufficiently low return loss to be described as an efficient antenna.

In order to estimate the heating effects of the antenna designs in a vessel, an associated specific absorption rate (SAR), as will be understood by those skilled in the art, can be calculated with Comsol (COMSOL AB, Sweden) modelling software which is a Finite Element Method (FEM) solver.

An example of such a SAR plot is given in FIG. 10A which is a diagrammatic side view representation of the antenna, inflated balloon with saline and iohexol 300 (1:1) in a vessel embedded in muscle.

As the magnitude of the electric field varies with distance from antenna, the specific absorption rate also varies. Since the SAR is a function of the magnitude of the electric field, the SAR decreases as the distance from monopole antenna increases. Given that an application is for use within ISR where a metallic sent is also embedded in the vessel wall an example of the impact was also made (see FIG. 10B) showing no negative shielding impact. Different dimension of antenna parameter may suit different balloon sizes for optimal SAR or an optimal common design may be used.

A comparison with non-microwave antenna-based heating such as heating using a resistive coil to heat fluid in the balloon, was made with a Comsol simulation model implementing a bioheating equation. FIG. 11A shows the poor distribution of heat into the vessel wall in comparison with FIG. 11B where the microwave antenna penetrates more quickly and with less thermal gradient that can lead to unwanted apoptosis.

Ex Vivo Testing

Having established the response of certain cell types in an in-vitro environment to a range of microwave intensities and durations, a prototype was constructed following the principles of the embodiments detailed previously (see FIG. 9B).

The prototype used was the same item tested with the VNA (see FIGS. 10A-10C) but now used in an excised bovine heart (see FIG. 12).

The catheter was fed into a cardiac artery and the balloon inflated by pressurising the saline and iohexol 300 (1:1) mixture with a syringe, much in the same way as a PTCA procedure in a human heart.

The antenna was powered by a microwave generator operating at 8 GHz. Temperature measurements were made using a fibre optic temperature probe, NOMAD-Touch (Qualitrol Company LLC, NY, USA) that is not influenced by microwave radiation in the way a metallic probe would be.

Temperatures were taken external to the balloon, on the external surface of the partially embedded artery on the heart muscle. Validation of ramp parameters, raising the temperature from the initial 37° C. to excess of 47° C. and 52° C., were made and the rate of change of temperature (see FIG. 13) was approximately 1.5° C./s at 10 W power and 1.7° C./s at 15 W power.

Maintaining the temperature of the tissues helps ensure the correct biological response and subsequent clinical outcome. The in-vitro experiments on various cell types demonstrated that low power microwave energy, 5 W or less was sufficient to maintain a temperature in its surroundings for a period of time.

Using the same ex-vivo bovine heart (see FIG. 12) to test the ramp parameters, the simulated PTCA procedure now used microwave power at 4 W or 5 W to maintain a temperature in a 2 C window for 60 s (FIG. 14), having already elevated the tissue with the system as illustrated in FIG. 13. Although the actual temperatures of 50 C and 43 C may not represent the desired therapeutic temperature, the ability to hold a temperature with acceptable tolerance can be inferred.

What is claimed:

1. A method of treating or preventing an arterial and/or vascular complication, said method comprising applying a heat treatment to an arterial and/or vascular tissue of a subject in need thereof, the method comprising:
    delivering microwave energy having a frequency of between about 5 GHz to about 15 GHz, wherein the microwave energy is delivered at a microwave power of up to 15 W to heat the arterial and/or vascular tissue of the subject at a rate of 1.5-1.7° C./s and to a temperature between about 40° C. to about 49° C., and then reducing the microwave power to between about 1 W to about 5 W to maintain the temperature of the arterial and/or vascular tissue of the subject between about 40° C. to about 49° C. for a period of time between about 15 s to 180 s.

2. The method of claim 1, wherein the arterial and/or vascular complication is a cardiovascular disease, peripheral arterial disease and/or peripheral vascular disease.

3. The method of claim 1, wherein the arterial and/or vascular tissue is a diseased and/or damaged arterial and/or vascular tissue.

4. The method of claim 1, wherein the arterial and/or vascular complication is a disease and/or condition selected from the group consisting of atherosclerosis; stenosis and some complication or effect associated with an existing treatment for the same, including restenosis.

5. The method of claim 1, wherein the subject in need thereof is a human or animal subject suffering from or predisposed and/or susceptible to a vascular or arterial complication.

6. The method of claim 5, wherein the subject in need thereof is suffering from a one or more selected from the group consisting of:
    (i) cardiovascular disease;
    (ii) atherosclerosis;
    (iii) stenosis;
    (iv) arterial/vascular occlusion; and
    (v) is susceptible or predisposed to any one of (i)-(iv).

7. The method of claim 1, wherein the subject in need thereof has been fitted with a stent.

8. A method of activating and/or priming/preparation an immune response within or in the vicinity of, an atheroma and/or atherosclerotic plaque, said method comprising applying a heat treatment to an atheroma and/or atherosclerotic plaque, wherein the heat treatment comprises:
    delivering microwave energy having a frequency of between about 5 GHz to about 15 GHz, wherein the microwave energy is delivered at a microwave power up to about 15 W to heat the atheroma and/or atherosclerotic plaque at a rate of 1.5-1.7° C./s and to a temperature of between about 40° C. to about 49° C., and then reducing the microwave power to between about 1 W to about 5 W to maintain the temperature of the atheroma and/or atherosclerotic plaque at between about 40° C. to about 49° C. for a period of time between about 15 s to 180 s.

9. The method of claim 8, wherein the immune response renders the atheroma, atherosclerotic plaque, or a cell or cells more susceptible to the action of a pharmacologically active agent as compared to an atheroma, atherosclerotic plaque, or a cell or cells not exposed to said heat treatment.

10. The method of claim 9, wherein the pharmacologically active agent is a systemic pharmacologically active agent, or an agent with local action.

11. A method of treating or preventing an arterial and/or vascular complication, said method comprising applying a heat treatment to an arterial and/or vascular tissue of a subject in need thereof, the method comprising:
    delivering microwave energy having a frequency of between about 5 GHz to about 15 GHz, wherein the microwave energy is delivered i) at a microwave power of 10 W to heat the arterial and/or vascular tissue of the subject at about 1.5° C./s to a temperature between about 40° C. to about 49° C., or ii) at a microwave power of 15 W to heat the arterial and/or vascular tissue of the subject at about 1.7° C./s to a temperature between about 40° C. to about 49° C., and
    then reducing the microwave power to between about 1 W to about 5 W to maintain the temperature of the arterial and/or vascular tissue of the subject between about 40° C. to about 49° C. for a period of time between about 15 s to 180 s.

* * * * *